(12) United States Patent
Baudat

(10) Patent No.: US 11,300,445 B2
(45) Date of Patent: Apr. 12, 2022

(54) SYSTEM AND METHOD OF WAVEFRONT SENSING WITH ENGINEERED IMAGES

(71) Applicant: Gaston Daniel Baudat, Glenmoore, PA (US)

(72) Inventor: Gaston Daniel Baudat, Glenmoore, PA (US)

(*) Notice: Subject to any disclaimer, the term of this patent is extended or adjusted under 35 U.S.C. 154(b) by 0 days.

(21) Appl. No.: 16/810,815

(22) Filed: Mar. 5, 2020

(65) Prior Publication Data

US 2020/0284649 A1 Sep. 10, 2020

Related U.S. Application Data

(60) Provisional application No. 62/814,196, filed on Mar. 5, 2019.

(51) Int. Cl.
*G06T 1/00* (2006.01)
*G01J 1/42* (2006.01)
(Continued)

(52) U.S. Cl.
CPC .......... *G01J 1/4257* (2013.01); *G06T 1/0014* (2013.01); *G06T 5/002* (2013.01); *G06T 5/50* (2013.01);
(Continued)

(58) Field of Classification Search
CPC .... A61F 2009/00848; A61F 2009/0088; A61F 2009/028; A61F 2/1613; A61F 2009/086;
(Continued)

(56) References Cited

U.S. PATENT DOCUMENTS 7,697,212 B2 * 4/2010 Jethmalani ............... G02C 7/02
359/652
7,780,294 B2 8/2010 Dai
(Continued)

FOREIGN PATENT DOCUMENTS

CN 103217871 A 7/2013
DE 102009058662 A1 6/2011
(Continued)

OTHER PUBLICATIONS

Yohei Nishizaki et al, "Deep learning wavefront sensing", Optics Express, vol. 27, No. 1, 240-251 (2019).
(Continued)

*Primary Examiner* — Jose L Couso

(57) ABSTRACT

A method of wavefront sensing with engineered images is provided with at least one wave receiving system. At least one desired parameter range is designated for the wave receiving system. At least one preliminary engineered image is then simulated to correspond with the desired parameter range. At least one inverse-model is then generated that outputs the desired parameter range by inputting the preliminary engineered image. A training process is then executed for the inverse-model to readily and accurately output the desired parameter range by inputting the preliminary engineered image. At least one measurement engineered image is then received in order to output at least one estimated parameter value for the wave receiving system with the inverse-model by inputting the measurement engineered image into the inverse-model.

14 Claims, 23 Drawing Sheets
(11 of 23 Drawing Sheet(s) Filed in Color)

(51) Int. Cl.
*G06T 5/00* (2006.01)
*G06T 5/50* (2006.01)

(52) U.S. Cl.
CPC ............... *G06T 2207/20081* (2013.01); *G06T 2207/20216* (2013.01)

(58) Field of Classification Search
CPC ..... A61F 2/1637; G06T 50/002; G06T 50/50; G06T 1/0014; G06T 2207/20081; G06T 2207/20216; G06T 2207/30041; G06T 2211/436; G06T 2219/008; G06T 7/0004; G06T 7/557; G06T 11/006; G06T 2211/424; G06T 2211/428; A61B 3/1015; A61B 3/0025; A61B 3/14; A61B 3/103; A61B 3/00; A61B 3/13; A61B 3/152; A61B 3/0075; A61B 3/028; A61B 19/00; G06F 3/0425; G06F 30/20; G01S 15/8993; G01S 15/89; G01S 15/8913; G01S 15/8931; G01S 15/8977; G01S 7/52003; G01S 7/52042; G01S 13/89; G01N 29/0654; G01N 29/262; G01N 29/348; G01N 29/4472; G01N 21/00; G01N 23/2055; G06K 9/20; G06K 2209/19; G06K 2209/40; G06K 9/0053; G06K 9/4628; G02B 2027/011; G02B 2027/014; G02B 2027/0075; G02B 2027/0172; G02B 26/06; G02B 21/0004; G02B 21/0092; G02C 2202/22; G02C 2202/06; G02C 7/028; G02C 7/024; G02C 7/027; G01M 11/0257; G01M 11/0292; G01M 11/0235; G03F 7/70133; G03F 7/70141; G03F 7/70191; G03F 7/706; G03H 1/0866; G06N 3/04; G06N 3/0454; G06N 3/08–088; G01J 1/4257; G01J 9/00; G01J 9/0215; G01J 9/00806; G01J 9/00804; G01J 2009/002; G02F 2203/18; G06V 10/143
See application file for complete search history.

(56) References Cited

U.S. PATENT DOCUMENTS

| | | | |
|---|---|---|---|
| 7,832,864 B2 | 11/2010 | Barrett et al. | |
| 9,182,289 B2 | 11/2015 | Barrett et al. | |
| 9,854,965 B2* | 1/2018 | Durr | A61B 5/7415 |
| 10,345,590 B2* | 7/2019 | Samec | A61B 3/024 |
| 10,624,612 B2* | 4/2020 | Sumi | G10K 11/341 |
| 2006/0007397 A1* | 1/2006 | Lai | A61B 3/1035 351/246 |
| 2008/0284979 A1* | 11/2008 | Yee | A61B 3/103 351/209 |
| 2010/0256967 A1* | 10/2010 | Smith | G01J 9/00 703/13 |
| 2011/0007270 A1* | 1/2011 | Sarver | A61B 3/1015 351/206 |
| 2018/0136486 A1* | 5/2018 | Macnamara | A61B 3/1015 |
| 2018/0177461 A1* | 6/2018 | Bell | A61B 5/0095 |
| 2019/0170575 A1* | 6/2019 | Caucci | G01J 1/0437 |
| 2019/0313904 A1* | 10/2019 | Dave | A61B 3/0285 |
| 2021/0080573 A1* | 3/2021 | Bachmann | G01N 29/262 |

FOREIGN PATENT DOCUMENTS

| | | |
|---|---|---|
| DE | 102009058663 A1 | 6/2011 |
| EP | 2653095 A1 | 12/2017 |
| WO | 2016154352 A1 | 9/2016 |
| WO | WO2019046550 A1 | 3/2019 |

OTHER PUBLICATIONS

A. Tokovinin et al, "Donut: measuring optical aberration from a single extra-focal image", vol. 118, No. 848, Astronomical Society of the Pacific.

* cited by examiner

SYSTEM AND METHOD OF WAVEFRONT SENSING WITH ENGINEERED IMAGES

The current application claims a priority to the U.S. Provisional Patent application Ser. No. 62/814,196 filed on Mar. 5, 2019.

FIELD OF THE INVENTION

The present invention generally relates to a system and method of wavefront sensing with engineered images. More specifically, the present invention is used to analyze an optical system with the engineered images.

BACKGROUND OF THE INVENTION

Wavefront (WF) sensing (WFS) is an important task to evaluate natural or artificial optical systems, such as lenses, telescopes, microscopes, cameras, optical assemblies, eyes, atmospheric turbulences, biometric data, etc. The analysis of the WF provides information about the system under investigations such as aberrations and its optical transfer function (system identification), among many other related figures of merit. WFS can be done in the context of coherent (or partially) coherent light (like with laser) or incoherent (broadband) light as well. FIG. 6 shows the general conceptual approach for identifying an optical system.

One very common approach on WFS is to use a planewave (PW), a point source set at infinity. For instance, this can be accomplished with an optical system, where a pinhole (i.e. source) is placed at the focal plane of a lens/optical system such its image is located at the infinity. Consequently, this image becomes the source for the WF analysis, a PW.

In astronomy, the source may be an actual star (i.e. which from a practical standpoint is a point source at the infinity) or an artificial star (e.g. a ground-based laser illuminating the upper atmosphere sodium layer). In the latter case, the wavefront is not a planewave anymore, however, the present invention can be applied to situations where the WF is not planar indeed.

For the identification of an optical system under analysis (estimation of its optical transfers function, aberrations, parameters, etc.), one studies the WF using some WF sensor usually placed at the optical exit. Comparing this WF (exiting the optical system) with the known incoming WF provides the necessary information for the identification of an optical system.

The WF sensor is a key element in this context, and common approaches for retrieving the WF are Shack Hartmann (SH) WF sensor, pyramidal WF sensor, and curvature sensing and phase diversity WF sensor, of which the last two being based on, at least, two defocused images at different locations in the optical path (usually before, at, and/or after the focal plane of an imaging optics).

An example would be the FWS of an actual star imaged by a telescope in the context of adaptive optics (AO). AO aims at canceling as much as possible the atmospheric turbulences, known as seeing that degrades the image quality taken by the telescope. One usually uses the short term WF to drive AO actuators shaping the scope optics (usually, deformable mirrors associated with tilt/tip correction devices) for compensating in real-time (in the milli-second range) the seeing. Longer term WF data (average over time) is used in the context of adaptative optics aiming to detect and compensate the scope optic aberrations due to flexure, temperature, alignment/collimation, etc.

In both cases (adaptative and adaptive optics), one assumes that the incoming light beam (starlight) is a PW resulting to a point spread function (PSF) at the scope focal plane (the image of the star). The WF sensor is place in the vicinity of the scope focal plane. In the most common configuration, the PSF is re-imaged as a PW and sent to a WFS, such as a SH. This WF is then compared with an expected PW. The discrepancies, if any, are used to infer the optical properties of the scope and the seeing, usually by the mean of Zernike polynomial decomposition. From there, actions are taken to correct/cancel the telescope aberrations, if any, and the seeing effect leading to a better, hopefully, diffraction limited (DL) images at the scope focal plane.

As stated above, one can use a natural star as a perfect point source at the infinity. The resulting PW can be used to identify the scope optics itself (aberrations if any), if one averages over time the seeing (several minutes) or stacks many short-term frames. This is known as a single pass identification. An actual star can be replaced by artificial one as well.

Another approach for a scope identification, or any others optical systems, would be to use a double pass approach in the lab with an optical bench or on the ground. In this configuration, the source (a pinhole) is usually placed at the scope (or optical system) focal plane resulting in a PW (if the scope is free of any aberrations) exiting the scope aperture. Consequently, one places a flat mirror of high quality in front of the scope aperture to reflect the PW which now travels in the opposing direction through the scope (or optical system) a second time, and hence the name of double pass analysis which in effect double the telescope (or optical system under investigation) aberrations. A WF sensor is then used to analyze the return WF like in the single pass approach. In either of these methods, the fundamental idea is to use a WF sensor near the scope (optical system) focal plane, for instance a SH WF sensor, which can be seen in FIG. 7.

So far, as an example, we have used a telescope to describe WFS application, but it should be understood that this does not limit in anyway the form or shape of the scope used in the present invention. It is just an example of application for the sake of explanation.

BRIEF DESCRIPTION OF THE DRAWINGS

The patent or application file contains at least one drawing executed in color. Copies of this patent or patent application publication with color drawing(s) will be provided by the office upon request and payment of the necessary fee.

DETAILED DESCRIPTION OF THE INVENTION

All illustrations of the drawings are for the purpose of describing selected versions of the present invention and are not intended to limit the scope of the present invention.

Overview

Figure 1:
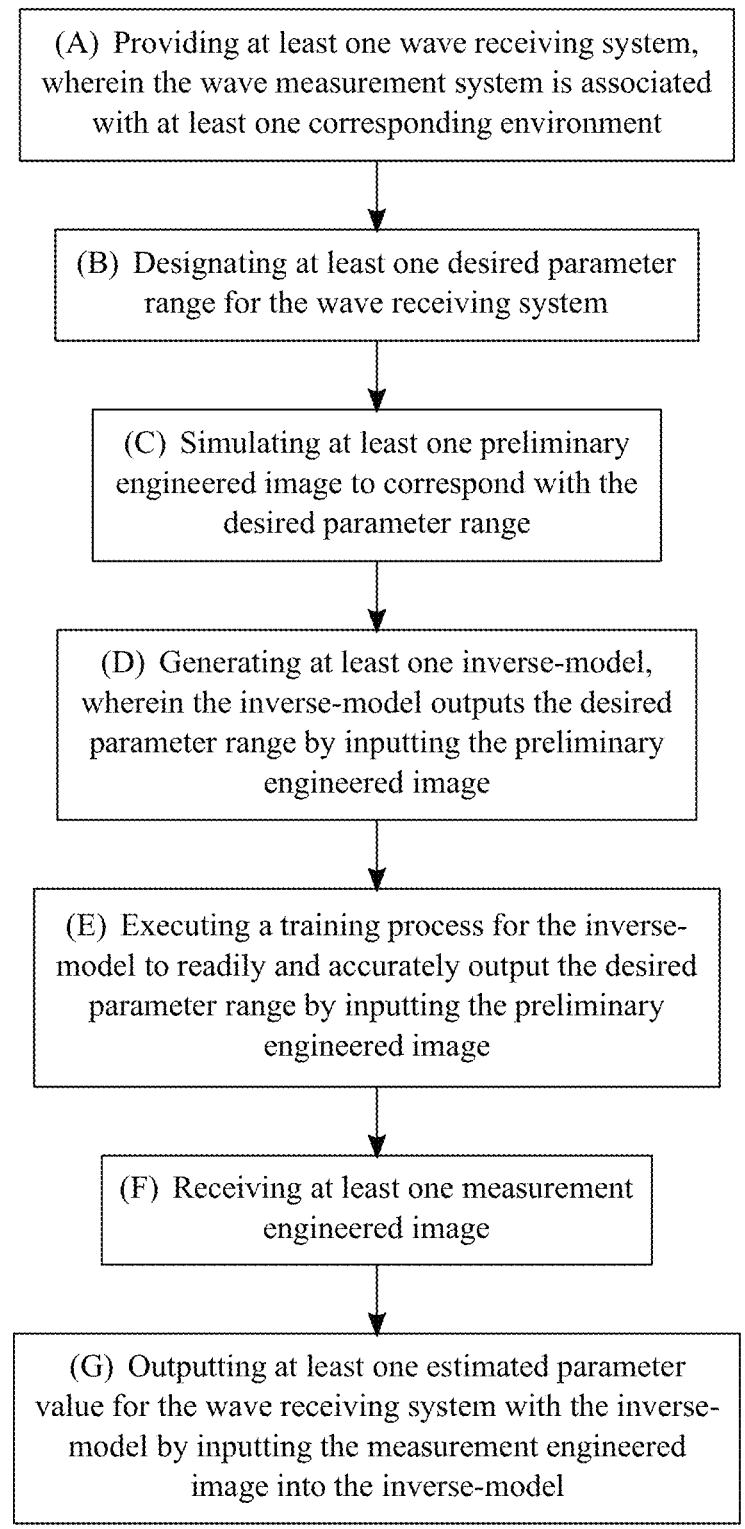
FIG. 1 is a flowchart illustrating the overall process for the method of the present invention.

As can be seen in FIG. 1, the present invention is a system and method of wavefront sensing with engineered images, which allows a user to identify and evaluate any major or minor malfunctions in a wave receiving system. Thus, the system of the present invention is provided with at least one wave receiving system that is associated with at least one corresponding environment (Step A). A wave receiving system is any system that is able to detect, measure, modify, and/or process information for physical waves, which include, but are not limited to, sound waves and electromagnetic waves. However, the present invention is preferably designed for the wave receiving system to be a natural or artificial optical system, such as telescopes, microscopes, cameras, eyes, and other optical assemblies. The corresponding environment is the immediate surroundings of the wave receiving system and may impact the analysis of the wave receiving system during the method of the present invention.

The overall process followed by the method of the present invention allows a user to identify and evaluate any major or minor malfunctions in a wave receiving system by wavefront sensing with engineered images. The overall process begins by designating at least one desired parameter range for the wave receiving system (Step B). A desired parameter range is a range of numerical data and/or a mathematical definition that assists a user in assessing the wave receiving system. The overall process continues by simulating at least one preliminary engineered image to correspond with the desired parameter range (Step C). The preliminary engineered image is an image that is created to relate to the desired parameter range and is used to initialize a computer model in the subsequent step. The preliminary engineered image may also account for noises. The overall process proceeds by generating at least one inverse-model that outputs the desired parameter range by inputting the preliminary engineered image (Step D). The inverse-model is simulation information for engineered images that include model input(s) and desired model output(s). In addition, the inverse-model may account for pre-processing, calibration, and/or noises. The overall process continues by executing a training process for the inverse-model to readily and accurately output the desired parameter range by inputting the preliminary engineered image (Step E). The training process is used to design, train, build, and test/validate the inverse-model with databases of simulated or actual data so that, if the preliminary engineered image is inputted into the inverse-model, then the inverse-model can effectively and efficiently output the desired parameter range. The overall process proceeds by receiving at least one measurement engineered image (Step F). The measurement engineered image is an image that is created to relate to the desired parameter range and is used to analyze a wave receiving system.

The overall process concludes by outputting at least one estimated parameter value for the wave receiving system with the inverse-model by inputting the measurement engineered image into the inverse-model (Step G). The estimated parameter value is a readable result that can be used to identify and evaluate any major or minor malfunctions in a wave receiving system. The estimated parameter value may be displayed, played, recorded, shared, processed, broadcasted, and/or analyzed by the present invention. The estimated parameter value may further be used to infer other information/data including, but not limited to, the Zernike terms to the wavefront (WF) or point spread function (PSF), modulation transfer function (MTF), ophthalmic data, seeing, noise, and optical design parameters. The estimated parameter value may further be used to prompt actions including, but not limited to, adaptive optics (AO), image enhancement, recognition/classification, risk management, predictive maintenance, auto-focus, guiding, and biometry.

An engineered image can be configured in a variety of different ways. One such way is to configure the preliminary engineered image and/or the measurement engineered image from a mean of defocusing in order to create the necessary distortion of an image. Another way is to configure the preliminary engineered image and/or the measurement engineered image from a mean of defocusing its respective image a mean of the wave receiving system while using at least one wave aberration element. The wave aberration element can be, but is not limited to, at least one refractive element, at least one reflective element, at least one diffractive element, or combinations thereof. Moreover, a parameter can also be defined in a variety of different ways. Thus, the desired parameter range and/or the estimated parameter value is defined by Zernike polynomials, Strehl's ratio, Seidel's aberrations, a point spread function, an optical transfer function, optomechanical data, ophthalmic measurement data, wavefront, or combinations thereof.

Figure 2:
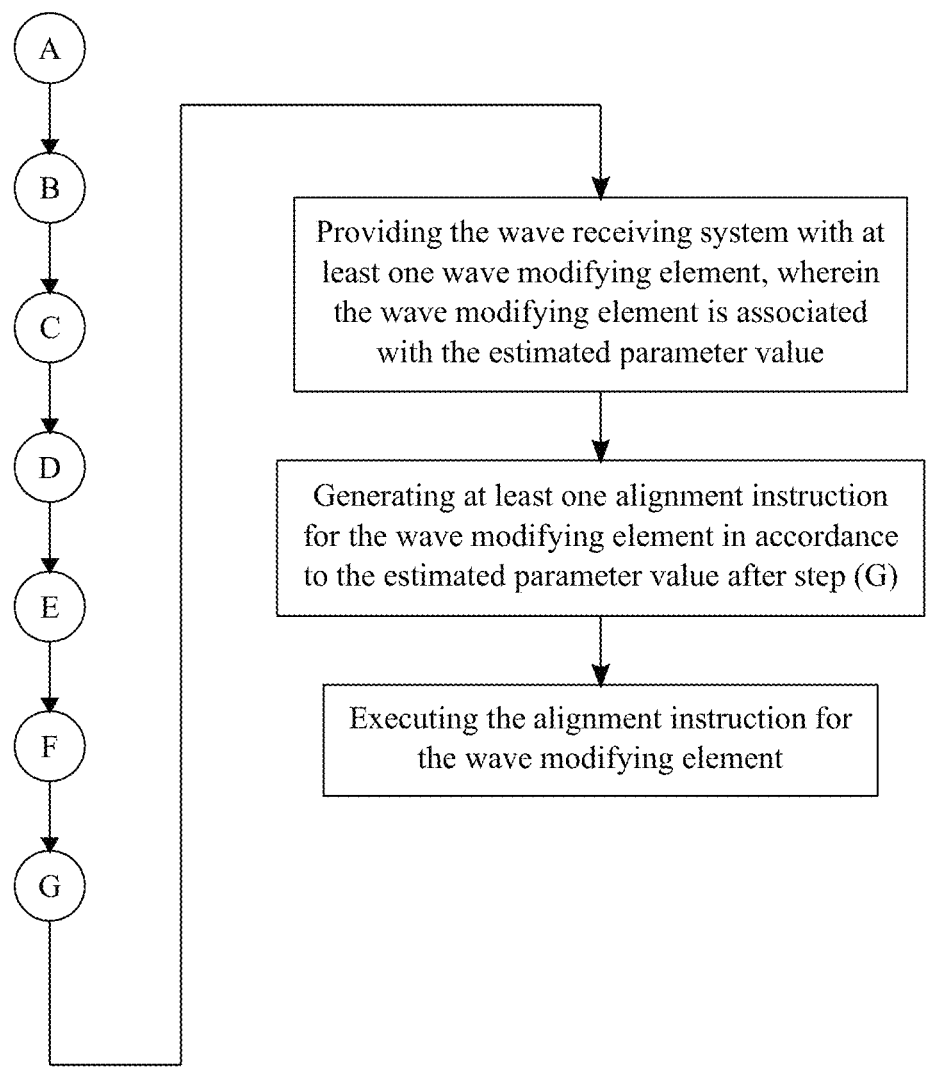
FIG. 2 is a flowchart illustrating the subprocess of aligning a wave modifying element on the wave receiving system for the present invention.

As can be seen in FIG. 2, one subprocess for the method of the present invention may be used to properly align the wave receiving system. Thus, the wave receiving system needs to be provided with at least one wave modifying element that is associated with the estimated parameter value. For example, if the wave receiving system is an optical system, then the wave modifying element can be an adjustment mechanism for the focal length of the optical system. This subprocess generates at least one alignment instruction for the wave modifying element in accordance to the estimated parameter value after Step G. The alignment instruction is an adjustment for the wave modifying element that would optimize the functionality of the wave receiving system. Again, for example, if the wave receiving system is an optical system, then the alignment instruction can be used to shorten or lengthen the focal length in order to bring the optical system into focus. Thus, this subprocess concludes by executing the alignment instruction for the wave modifying element, which physically adjusts the wave modifying element within the wave receiving system.

Figure 3:
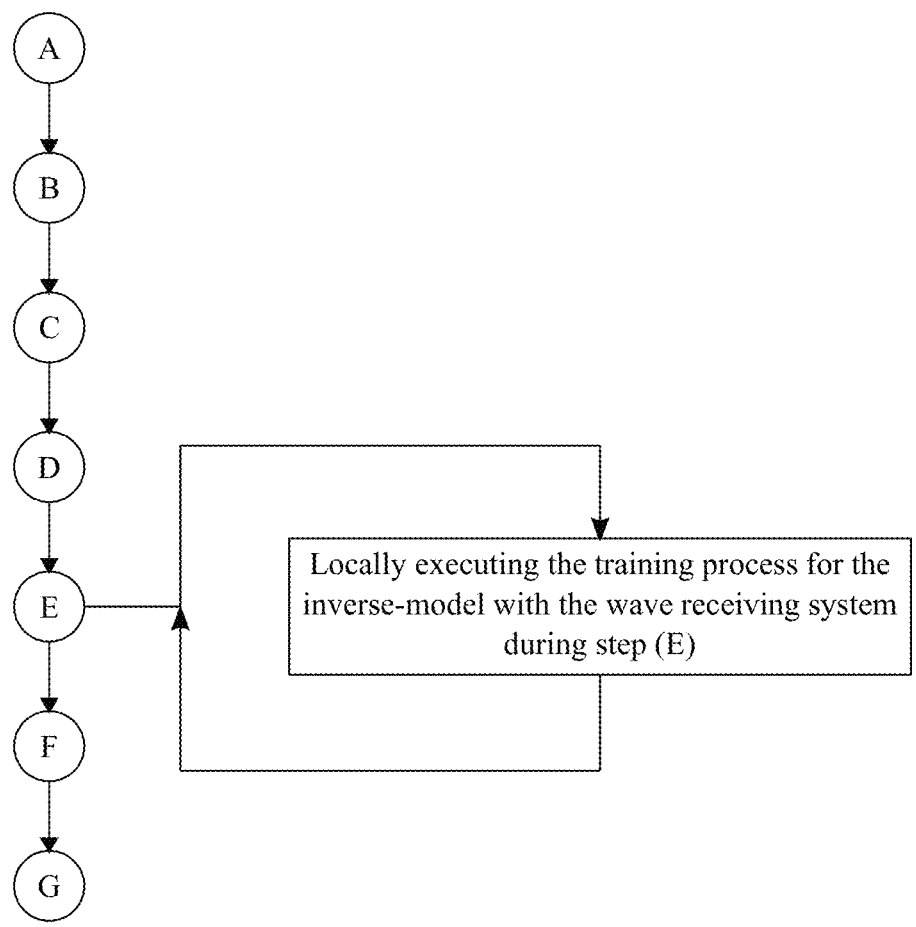
FIG. 3 is a flowchart illustrating the subprocess of locally training the inverse-model.
Figure 4:
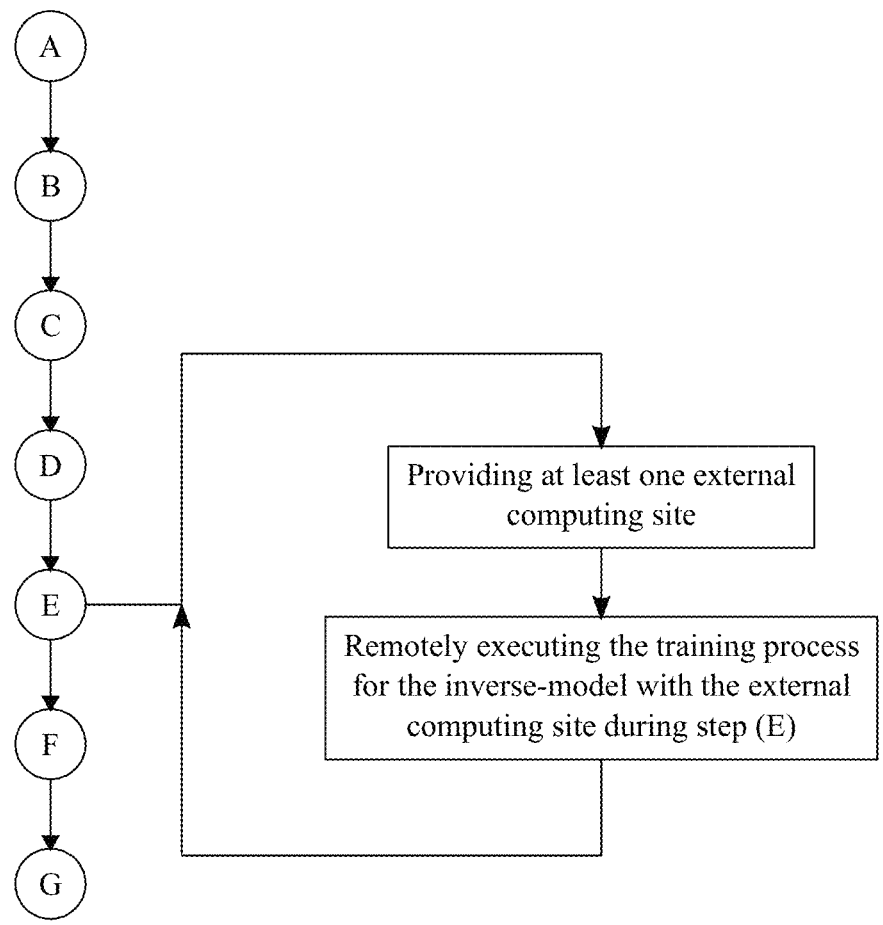
FIG. 4 is a flowchart illustrating the subprocess of remotely training the inverse-model.

The training process for the inverse-model can be configured in a variety of different ways. As can be seen in FIG. 3, one way is to locally execute the training process for the inverse-model with the wave receiving system during Step E so that the training process would readily have available all of relevant information for the wave receiving system with the corresponding environment. As can be seen in FIG. 4, another way is to remotely execute the training process for the inverse-model with at least one external computing site during Step E so that the training process would be able to access a larger amount of reference material. The training process for the inverse-model may also be based on different types of computing including, but not limited to, edge computing, stream computing, cloud computing, batch computing, or combinations thereof.

Figure 5:
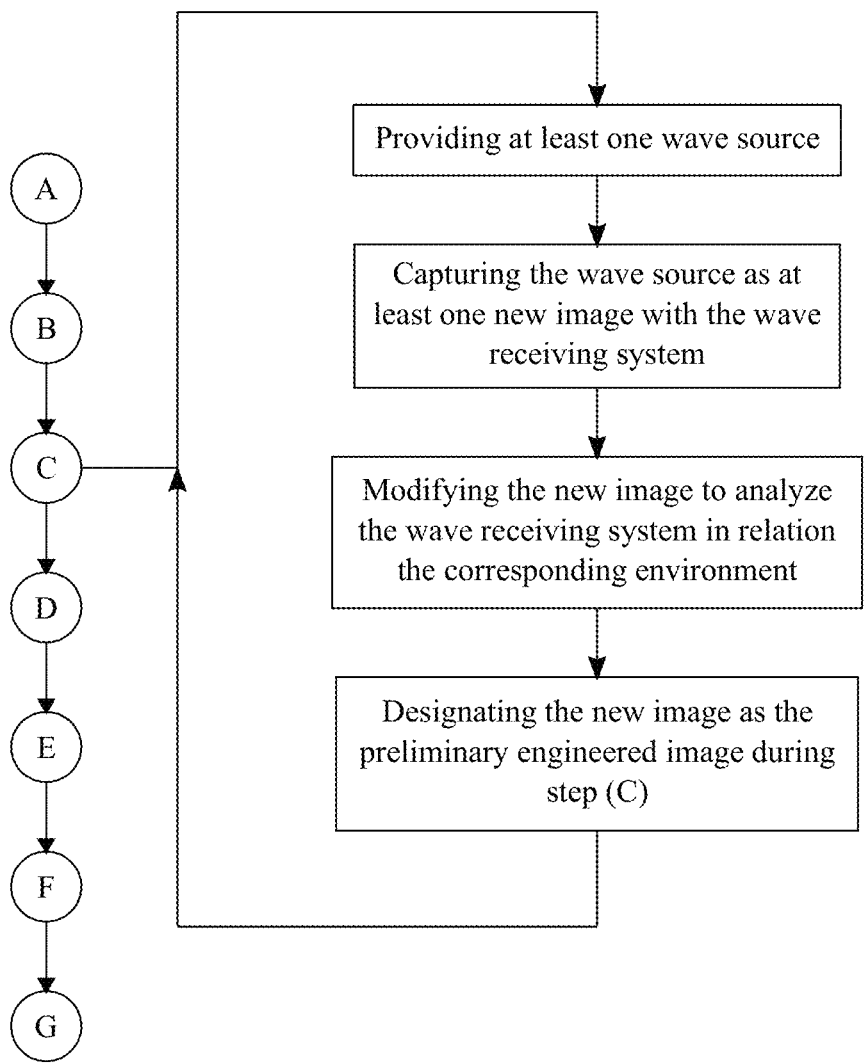
FIG. 5 is a flowchart illustrating the subprocess of creating an engineered image.

As can be seen in FIG. 5, another subprocess for the method of the present invention may be used to create an engineered image. Thus, at least one wave source is provided by the present invention. The wave source is the point of origination for the physical waves encountering the wave receiving system. For example, if the wave receiving system is a telescope, then the wave source could be a star. The wave source can be configured as a point source or an extended source. The wave source can also be generated by a natural source or an artificial source. The wave source can also be made of coherent light or incoherent light. Moreover, this subprocess begins by capturing the wave source as at least one new image with the wave receiving system so that the new image is the raw data depicting the wave source. The subprocess continues by modifying the new image to analyze the wave receiving system in relation the corresponding environment so that the new image incorporates physical characteristics of the wave receiving system into the modified data depicting the wave source. The subprocess concludes by designating the new image as the preliminary engineered image during Step C, which allows for the creation of an engineered image.

WFS, from the Image Intensity to the WF

Figure 8:
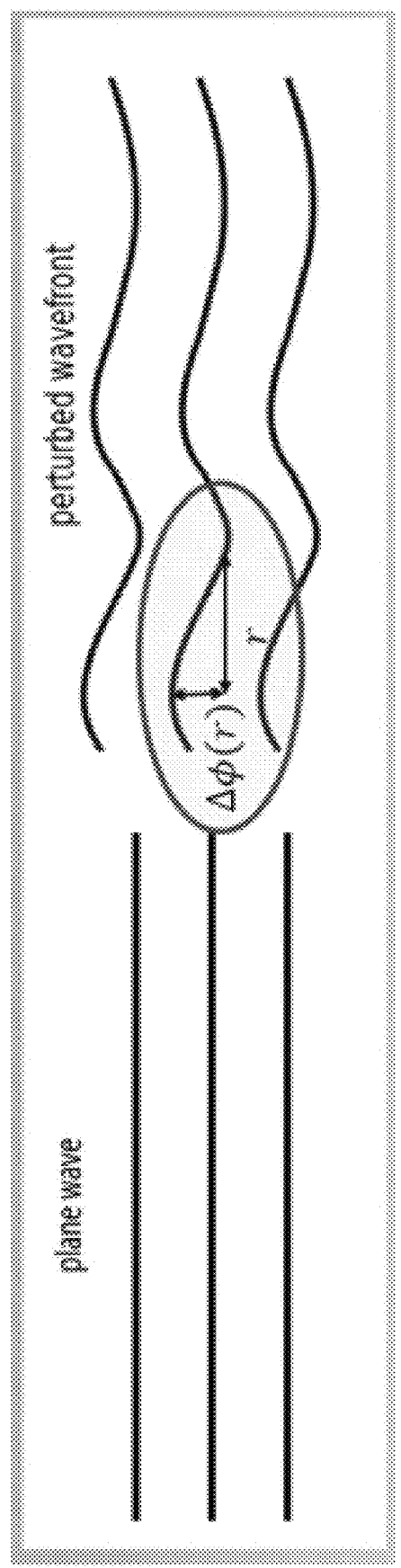
FIG. 8 is a diagram illustrating a planewave versus a perturbated wave and the phase difference.

The WF is usually described by the light phase, mainly the relative phase, across the aperture used for the analysis. The absolute phase (known as the piston, or the Zernike term/coefficient (Z0)) is only relevant, if any, in the context of coherent light. FIG. 8 shows a PW and a perturbated (aberrated wave) with some phase difference $\Delta\phi$ (at a given location inside the aperture).

Figure 7:
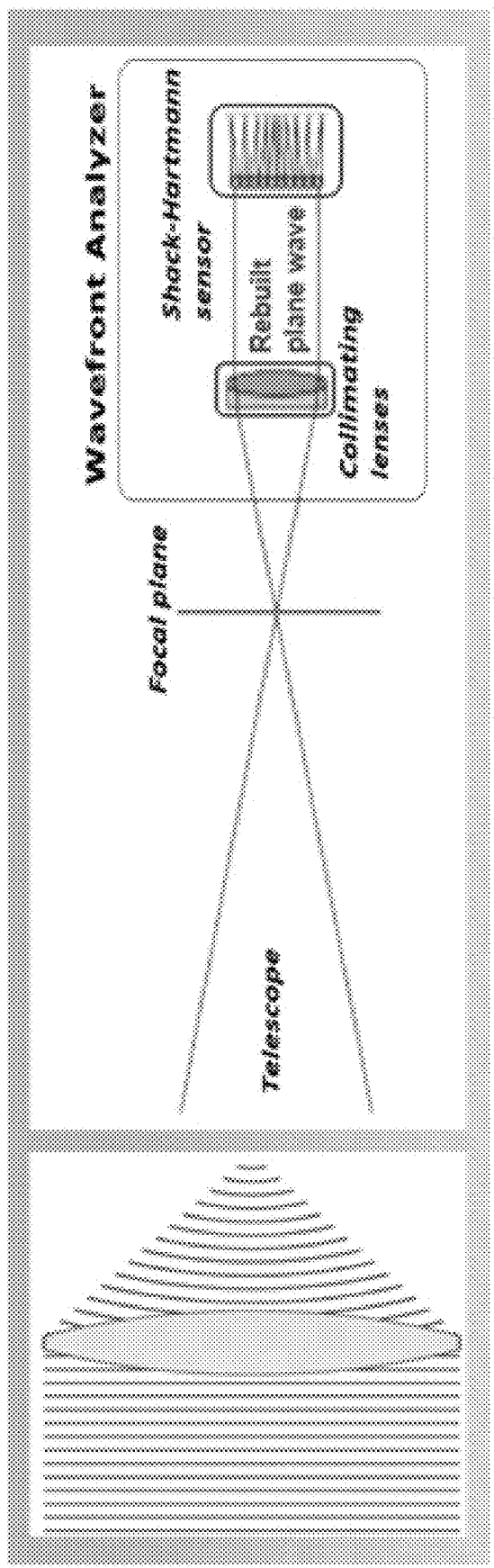
FIG. 7 is a diagram illustrating a telescope analysis using a Shack Hartmann wavefront sensor.

Electromagnetic waves, especially light, have too high frequencies for a direct measurement of the phase. To infer the WF phase (absolute or relative), one can use interferometry or compute phase retrieval from the intensity of the light pattern, usually, at or near the focal plane of an optical system. This can be done directly with the same optical system under analysis (identification) or with the use of a secondary optical system for imaging the WF. For instance, an SH WF sensor may use a collimator (a convergent lens) to re-image the incoming converging beam of a telescope as a PW before the SH WF sensor micro-lens array, which is shown in FIG. 7.

Figure 9:
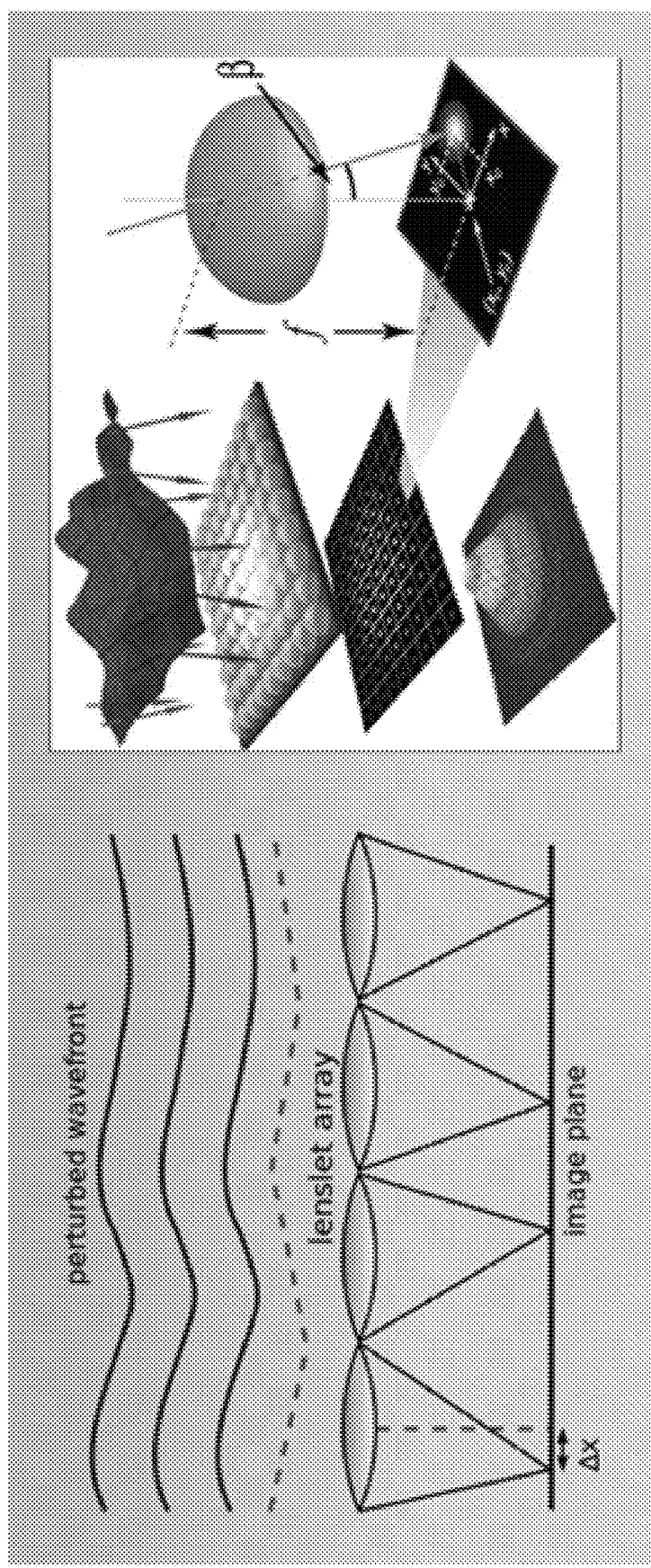
FIG. 9 is a diagram illustrating a Shack Hartmann wavefront sensor using a micro-lens array to analyze a wavefront.

In either of these cases, the WF phase is inferred from the image intensity or geometry pattern. In the SH context, each micro-lens creates its own image (i.e. PSF) of the incoming PW at different locations on the sensor plane (e.g. a CCD or CMOS camera). The relative motion (in the X and Y directions on the sensor plane) of each of those images (centroids) is used for retrieving the local FW phase derivative, which is seen in FIG. 9. A modal reconstruction of the wavefront is usually carried out using the Zernike polynomial decompensation over the unit circle associated with a linear regression to fit a direct model through the data.

Pyramidal WF sensors are similar in concept looking at the derivative of the wavefront. On the other hand, curvature and phase diversity WF sensors are based on the comparison (usually through a difference) of at least two defocused PSFs. Both use the irradiance transfer differential equation to infer the phase from the difference of PSF light intensities. It has been shown that a single defocused PSF contains all the necessary information for reconstructing the WF. This technique may require a reference PSF, for instance, taken from a long-term averaging of the PSF when working under seeing limited conditions and/or taken from a local spatial normalization of the image intensity in the sub-aperture used to sample the PSF.

It should be understood that, when we refer to PSF normalization, it could be a normalization using the current PSF information (e.g. local or global amplitude normalization or any other suitable normalization using the current PSF data), the difference with a reference/expected PSF (i.e. either recorded under known conditions or calculated), or a combination of both approaches (i.e. PSF normalization and difference with a reference PSF).

Seeing scintillation cannot be canceled out with a single PSF approach, however, one can use a long exposure to average out the seeing and still recover most of the Zernike terms. Scintillation is usually not an issue when analyzing an optical system in the lab under a control environment for which we may set the SNR at a required level by increasing the light intensity and/or the integration time of the sensing camera.

On the above approaches, one usually works with a PSF resulting from an incoming PW. In the context of curvature sensing and phase diversity, one can use defocused PSFs for phase retrieval and WF reconstruction. Thus, the present invention includes a new approach for phase retrieval and WF reconstruction from at least one engineered image. Defocused PSFs are just a possibility among many.

WFS Using an Engineered Image

The present invention includes a new approach to infer/extract the WF information (such as, but not limited to, the Zernike coefficients) from at least one engineered image.

Curvature sensing and phase diversity methods use defocused PSFs, which can be seen as engineered images with some known level of optical aberration explicitly induced (i.e. defocus) in order to recover the phase. WF reconstruction from an in-focus PSF (light intensity) is an ill posed problem because, since there is an ambiguity in the phase, and since the light intensity of the PSF results from the squared of the WF Fourier transform amplitude, the phase information content is generally lost. For instance, a focused PSF, remains identical if the Zernike term/coefficient signs are changed (Z0, Z1, Z2, and Z3 set to zero) while their magnitudes are kept unchanged. To recover the phase information from the PSF (light intensity), one needs to add some level of prior (known) phase distortion, like defocus.

The present invention considers the general concept of processing an engineered image resulting from the interaction between some source (artificial or natural) and an optical system as well as a WF sensor. The image seen by the WF sensor camera has been engineered in order to retrieve the WF without any ambiguity, as discussed above. A defocused PSF is one example of such an engineered image. In this case, the image is simply engineered by placing the WF sensor camera at some distance from the focal plane of an optical system. The WF sensor in such case is usually just a simple camera, without any optics beside a window the protect the sensor.

Figure 10:
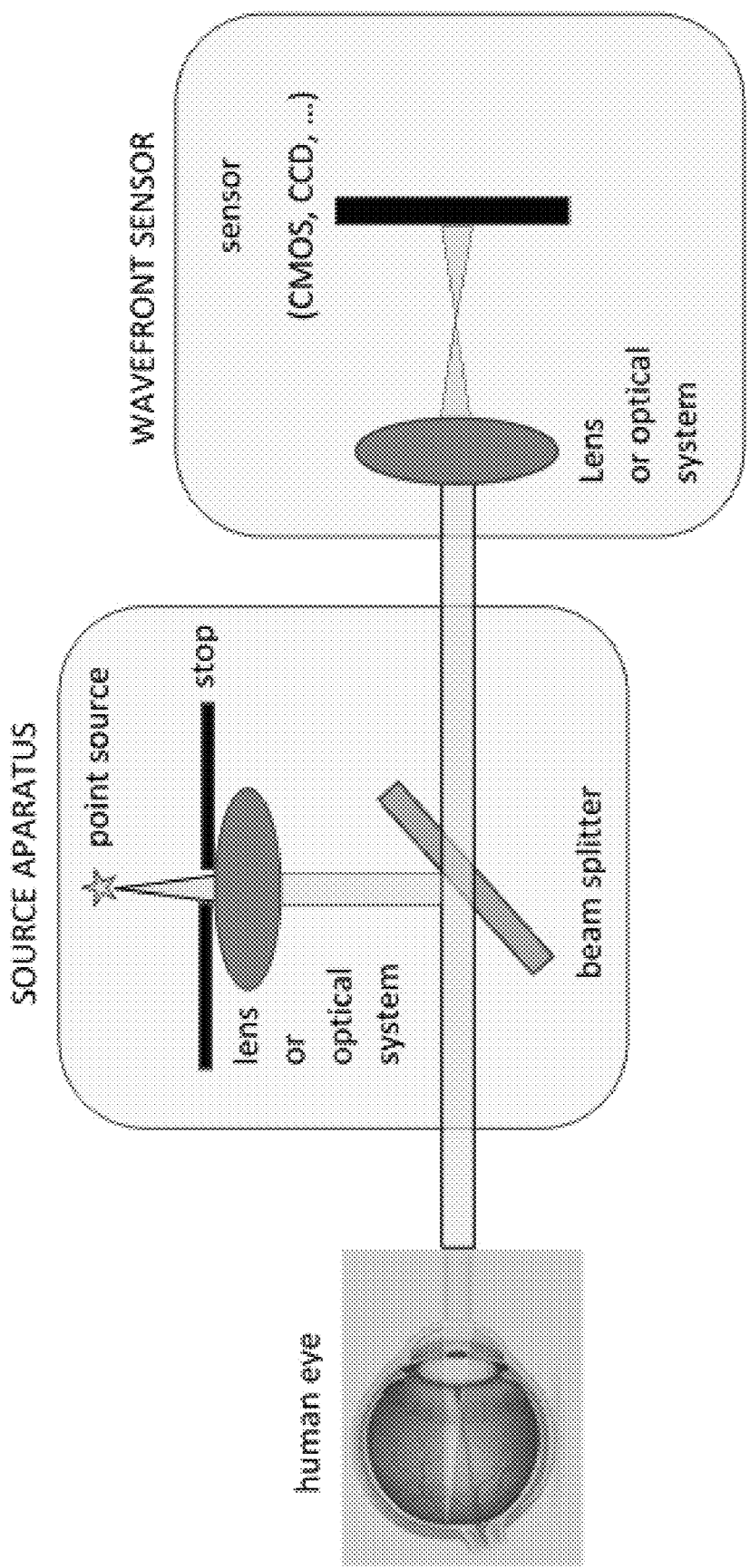
FIG. 10 is a diagram illustrating a source apparatus and wavefront sensor using a defocus point spread function for an optical analysis of the human eye, wherein a point source is imaged as a planewave which in turn is re-imaged by the human eye as a point spread function (with or without some aberration), and wherein this image becomes a source and then a planewave (or close, depending of the eye aberration, if any) which is used by the wavefront sensing for which the point spread function (engineered image) has been defocused.

However, if the optical system under analysis does not provide any image (it is not an imaging setup like a telescope), one can add the necessary optics (source and/or imaging optics) in front of the WFS camera for producing an image with the required properties. That would be the case in the context of measuring aberrations of an eye for instance, which is shown in FIG. 10. In such situations, the WFS is composed of more elements, beside its camera, in order to engineer an image to this camera.

It should be understood that one may have to do some calibration of the WFS (and/or source), at least once, in order to compensate for known optical/system aberrations, if any. This can be done with a known source (like a pinhole) and/or a reference device such as a good flat (or not) mirror, or by any relevant means.

Usually, when measuring the PSF of an optical system (e.g. telescope), one assumes that the source delivers a PW. However, there are applications for which this is not easily possible nor desirable. Also, one may want to use different WF, beside a PW, for the source in purpose for engineering (shaping and designing) the WFS image.

Also, the source does not need to be a point source. The point source could also be made of many point sources at different locations with different optical properties. The point source could also be an extended source(s) of any pattern, shape or form, or any combinations thereof. As a general approach, the engineered image seen by the WFS camera/sensor can be engineered by combinations of both the source and/or the WFS contributions (using the necessary apparatus, such as an optical system and/or mechanical defocus). Optical systems for engineering such image includes, but not limited to, at least one refractive element, at least one reflective element, at least one diffractive element, and combinations thereof.

As an example, assume one wants to analyze the quality (through WF analysis) of a lens system for a camera (DSLR, smartphone, etc.) set to focus at infinity (some camera systems may not have any focus control beside infinity, or set for a known source distance). The source could be designed such it appears located at some finite distance from the optical system under analysis, in this case as a lens and a camera/sensor (DLSR, etc.). The resulting source WF will be spherical. This configuration considers the lens and the camera as the FWS directly without the need of any other hardware.

Figure 11:
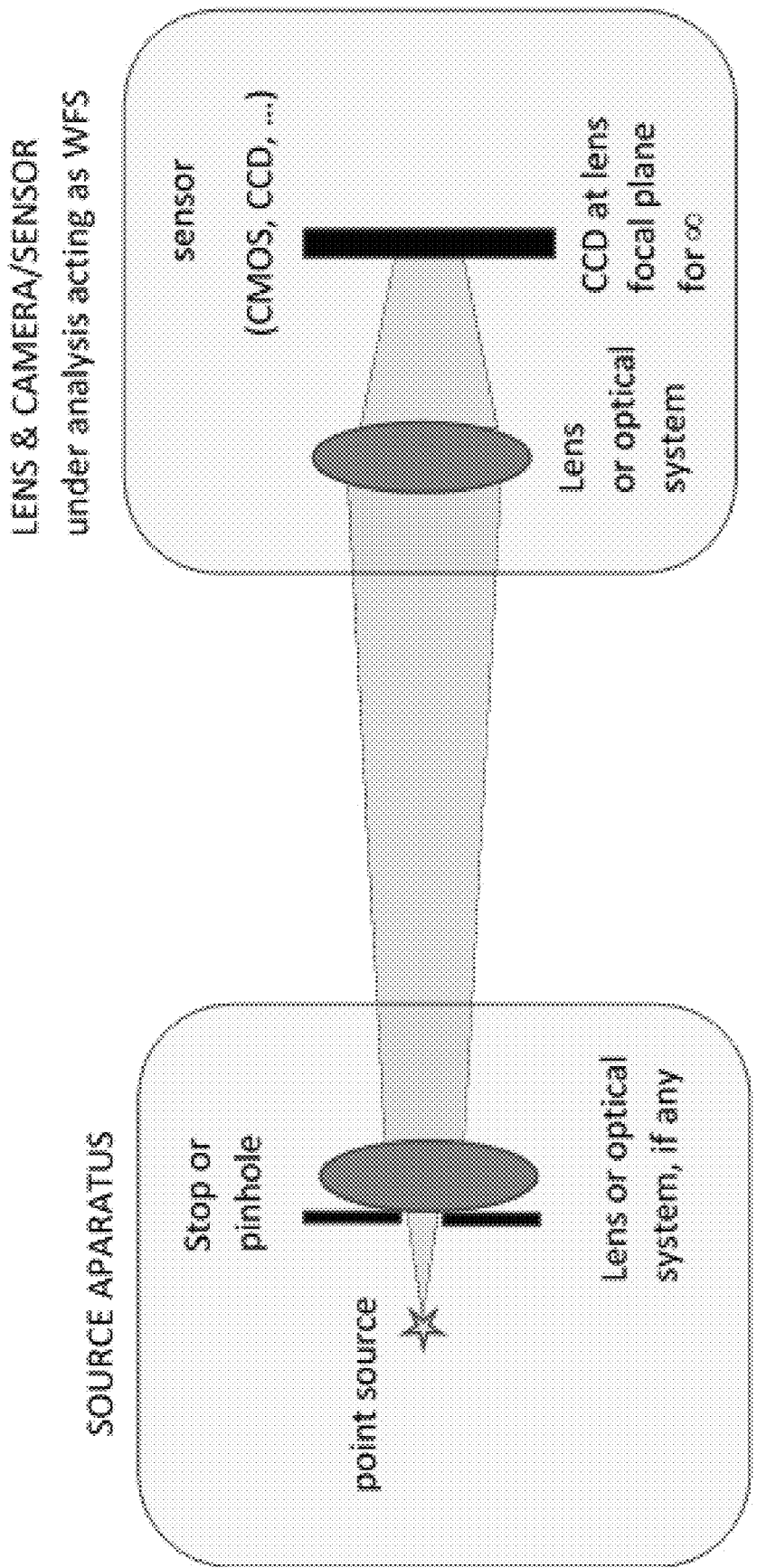
FIG. 11 is a diagram illustrating a lens and a camera/sensor under wavefront analysis using a spherical (divergent) wavefront from the source in order to engineer the image seen at the camera focal plane set for infinity.

The image seen by the lens and camera assembly under analysis will be defocused when the lens and camera is set to focus at the infinity. This result on an engineered image recorded by the camera under analysis. This engineered image is the lens and camera system defocused PSF with spherical aberration due to the finite distance of the source. By knowing both the defocus and the spherical values (Zernike terms, Z3 and Z8 for instance), one can use the engineered image for the WF reconstruction without any ambiguity. This approach is simple, fast, and low cost since it only needs an adequate source. FIG. 11 illustrates the concept disclosed here for a lens and camera analysis.

An assumption is that the camera under analysis was focused at infinity. Other situations could also be considered where the camera is focused to any given source distance, and the source is located to another distance such that the PSF will be defocused (with maybe some level of spherical aberrations or other kinds of aberrations).

In the telescope situation discussed before, this is a case where the source is located at infinity, and the sensing camera is offset from the scope focal plane to create a defocus. Although defocusing with a simple mechanical offset between the focal plane of the scope (any imaging optical system) and the sensing camera (using for doing WFS) is a simple solution, this can be archived by the mean of optical elements (reflective, refractive, diffractive, etc.) in front of the sensor too.

It should be understood for the present invention that the engineered images used for WF reconstruction may have been preprocessed/filtered, beside some signal level calibration/normalization, if any, (as discussed before) in order to remove sensor artifacts such as hot pixels, pixel gain variations, distortions, fixed pattern noise, etc. This usually implies using flat, bias, and dark frame processing applied to the engineered images before it can be used for WF reconstruction.

Wavefront Reconstruction from, at Least, a Single Engineered Image

Figure 6:
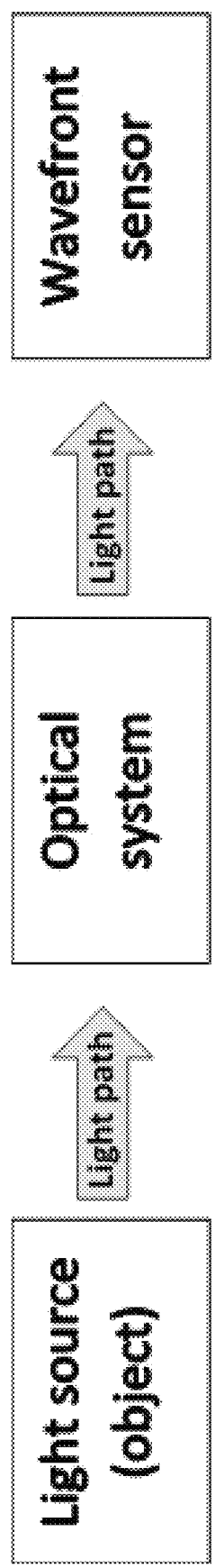
FIG. 6 is a diagram illustrating the identification of an optical system by using wavefront sensing.

The present invention addresses the reconstruction of the WF and therefore addresses the estimation of the optical system under analysis aberrations, if any, and performances, such as Zernike terms, Strehl ratio (SR), and others. To achieve this goal, this approach uses at least one engineered image for which the engineering operation applied to the whole system is known. The general approach is illustrated in the FIG. 6 where the engineering image(s) aspect is performed at either, or at both, the source and the WFS. It should be understood that FIG. 6 is a conceptual representation in the real setup the source that maybe is located inside the optical system under analysis, or on the same side than the WFS, as discussed in the double pass situation for telescope or for the eye wavefront analysis as can be seen in FIG. 10. The WFS could also be part of the optical system under consideration like that was disclosed on the above lens-plus-camera analysis as can be seen in FIG. 11 where the camera sensor is de facto used for the WF reconstruction. The same is valid for the engineering aspect of the image, which can be done (like defocus) by the system under analysis itself.

In the approach outlined by the present invention, the reconstruction of the WF (and all the other steps and processing resulting from it), from at least one engineered image from the system under analysis (including the source and WFS), is performed using only mathematical models of the engineered images, which are computed beforehand.

There is no need to acquire any actual engineered images from a given system for the only purpose of building the mathematical models used in the subsequent wavefront analysis of a given (or other) system. Engineered (or other) images/data could be used for preprocessing the data for calibration and conditioning/filtering purpose, if any, at the time that the analysis is performed. However, those images do not need to be part of the process to build the mathematical models used to reconstruct the WF. Therefore, the methods for the present invention do not need any data collection from any actual physical hardware and/or optical systems for building the mathematical models. If any actual system data (images or any other pertinent system data) is provided, it would be mainly for the sake of calibrations/tests and preprocessing.

Although, if the following for doing such WFS and reconstruction using a single engineered image, it should be understood that is not in any way, form, or shape a limitation and that several engineered images could be taken for a given analysis in order to mitigate errors, noise, and/or improve the results (like in the case of curvature sensing, or phase diversity, using at least two defocused images). Those engineered images may or may not be engineered the same way. In any case, the nature of the image engineering used is known beforehand and used to build the mathematical models used for the reconstruction of the WF, among things, from those engineered images.

Phase diversity (PD) and curvature sensing (CS) approaches use direct mathematical models for retrieving the WF, usually the Zernike coefficients. Those models (e.g. the irradiance transfer differential equation) require nonlinear optimization techniques, often in the form of iterative algorithms. Such methods are known to face some challenges (mathematical and numerical) like local minima (or maxima) or convergence issues of the optimization objective function. Such methods may also require substantial compensating mathematical mechanisms to improve the algorithm convergence and resulting accuracy. Such methods usually work best for small aberrations too. Finally, such methods assume simple defocused PSF images, using other engineered images (other types of aberrations) may prove intractable. One example would be, if in front of the WFS module, one places a diffractive structure (like a mask) or a some refractive/reflective optics and/or combinations of both. Those optics apparatus may be useful, or natural, for a given problem but very hard, if even possible, to find any direct model.

The present invention uses an inverse model approach. After calibration and preprocessing of the engineered image(s), if any, the data is fed to the inverse-model(s) which directly outputs the reconstructed wavefront, among things, in the form of the Zernike coefficients, or any other relevant ways, like the WF phase inside the pupil itself, the PSF, the Seidel aberrations, ophthalmic data, the optical alignment/collimation data, the Zemax parameters of the optical system under analysis, etc. The inverse-model(s) does not need, also it could, nor uses any knowledge of the optical system related physical equations (like the direct models do) to learn how to do a WF reconstruction, among things. Instead, the methods use machine learning techniques like, but not limited to, artificial neural networks (deep learning or others), support vector machines, feature vectors and regression machines, multivariate statistics, or any other machine learning approaches and combination of those.

The learning process is done using usually only simulated engineered imaged from a given optical system (including knowledge of the source and the WFS apparatus and the engineering process applied to the images). Therefore, such approach can easily work with many kinds of engineered images (beside simple defocused PSFs used with PD and CS) and under quite demanding/challenging situations like seeing limited conditions for an Earth based telescope, or noisy sensors (dim signal). Such perturbation can be simulated and introduced in the learning database too. If necessary, data could be taken from actual physical systems too. However, a computer simulation of the engineered image is unusually the preferred approach since one can build as many as we want (including noise, perturbations, etc.) without spending the time and money to acquire them from any physical apparatus, assuming it is even possible to do so. Although, some actual images (from a physical system) could mainly be used for calibration and preprocessing purpose (like flat, dark and bias frames).

The inverse-model(s) is trained with many different simulated (or actual or a combination) engineered (maybe millions) images (including noise and distortions, if any) to cover a given range of expected aberrations/distortions or any other relevant figures of merit. One can also simulate and build the model(s) for one wavelength or many, and/or also combine single wavelength models for simulation of polychromatic optical systems.

The simulated engineered images can be chosen at will to make the inverse-model(s) optimized for some tasks, like the accurate detection of some aberrations versus others, and/or the calculation of some parameters/figures of merits, like the Strehl ratio, or the seeing (Fried's parameter, r0) in the case of astronomy. As a matter of fact, one can use the simulated images along with their relevant desired/related outputs (Zernike, Seidel terms, PSF, WF, seeing, noise estimations, . . . ) to compare various engineered image strategies. From those various configurations using different engineered images and desired outputs, if any, a computer program may decide/infer, based on some metrics (some measures of accuracy or any other relevant figures of merit), which approaches would be the best for a given optical system and/or provides the user with information about those approach performances. This allows to select the best engineered image solution for a given problem without the need to build nor measure any physical optical systems.

Because the inverse-model(s) can be learned from simulated data, one has a lot of possible options available to compare with. There is also no need to know nor use any direct model (theoretical knowledge of the system is not required, although it could be used) to be able to use any of those various approaches (engineered image and related output). Also, the methods may use more than one inverse-model at the time, each specialized for a given task, or even for a given aberration and/or figure of merit, and/or subset, or for optical system design parameters, such as Zemax.

In some cases, a given inverse-model (or models) can cover a very large range of optical systems (like telescopes). In other cases, one may learn and tune the model(s) for a given optical system (including the source, natural and/or artificial, WF sensor, and the related engineering processes for making the engineered images) at will. Those multi inverse-models, if any, can be combined in series, parallel, or both. Those multi inverse-models can also be trained one at a time, all together, or combinations thereof including retraining some or all of the inverse-models after some have already been independently trained.

Figure 12:
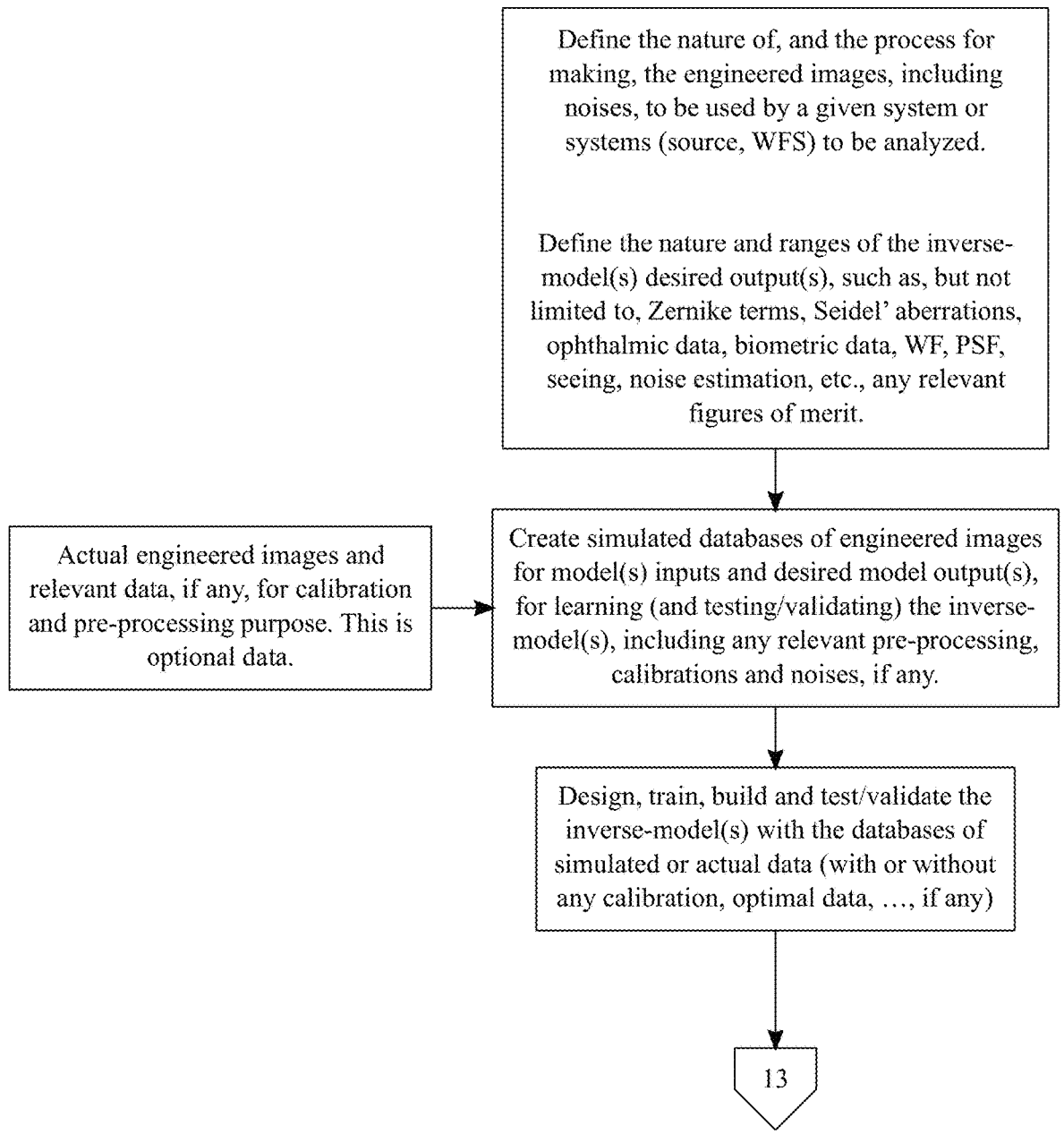
FIG. 12 is a diagram illustrating the conceptual process of wavefront sensing using engineered images.
Figure 13:
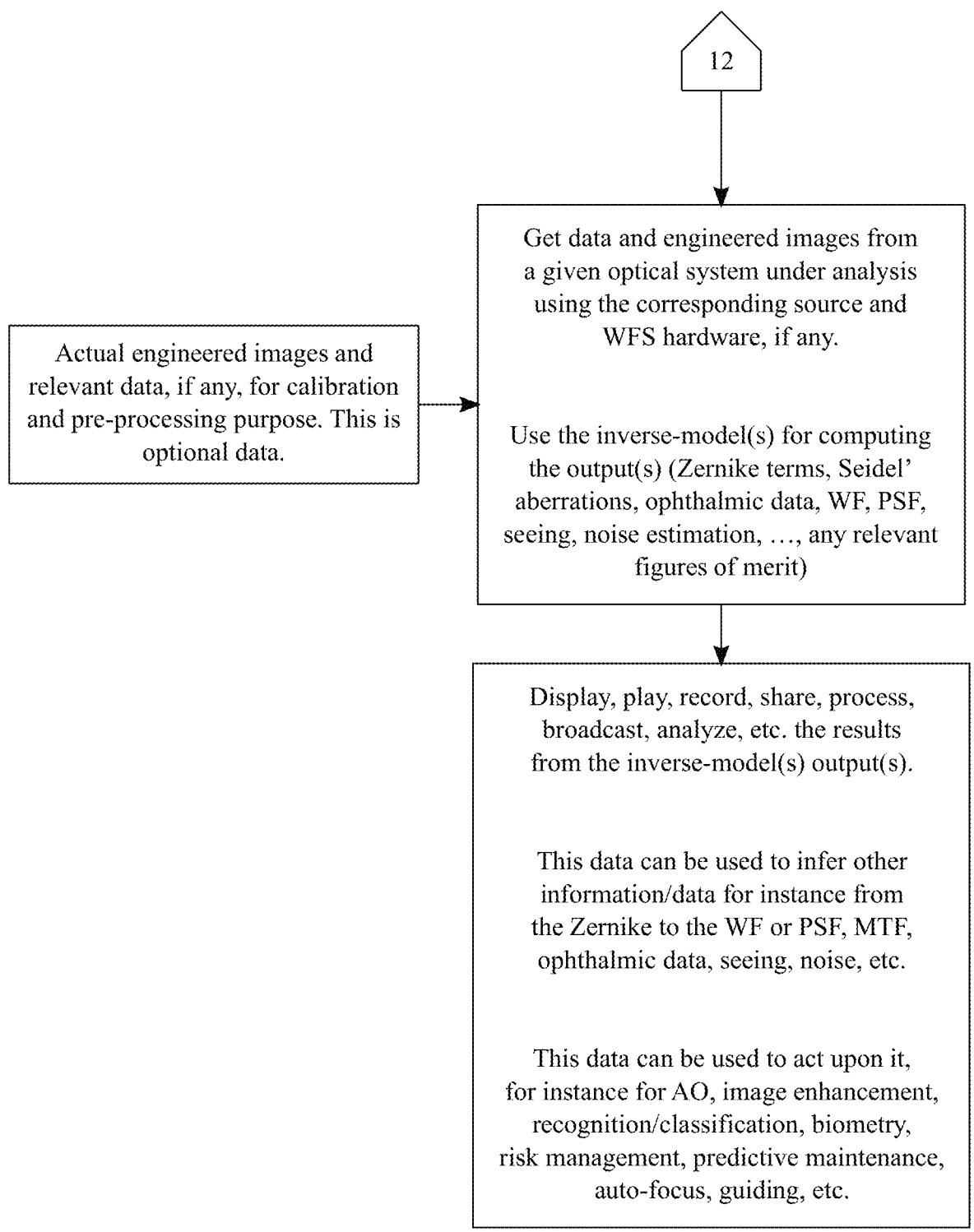
FIG. 13 is a continuation of FIG. 12.

The inverse-model(s) can be built and be trained either offline (batch processing) or online, on spot, locally (stand-alone), by edge computing, by using remote computing power such as "cloud" computing, by streaming, or combinations thereof. For instance, in some cases/applications, the inverse-model(s) may be built (from simulated engineered images and maybe some calibration data) on demand in the field (and/or lab) while in the process of performing an analysis. In other cases, the inverse-model(s) is available beforehand. In yet a different case, the engineered images along with a description (and maybe calibration data) of the optical system (including source, WFS, and the engineering process used for making the engineered images) may be recorded (live or not) and send/used off-line to build the inverse-model(s) and to perform an analysis of an optical system, for instance remotely, as a service. This could be conveniently done using the Internet for sending the data, or by using any other means to send and share the data, including parallel computing across many computers and/or networks, edge computing, streaming, etc. Inverse-model(s) can be trained and/or used with special/dedicated hardware machines, such FPGA or similar relevant hardware. The inverse-model(s) of the present invention usually does not, by design, require any iterative optimizing steps (the models can be built from a learning process beforehand) for analyzing an optical system. Therefore, it is well suitable for demanding real time applications, such as adaptive and adaptative optics. The present invention is conceptually summarized, as much as possible, in FIGS. 12 and 13.

The output(s) of the inverse-model(s) for a given optical system(s) under analysis/test can be used to display, play, record, share, process, broadcast, analyze, etc. the results from the inverse-model(s) output(s). This data can also be used to infer other information/data for instance from the Zernike terms to the WF or PSF, Modulation Transfer Function (MTF), ophthalmic data, seeing, noise, optical design parameters (Zemax), etc. This data can be used to act upon it as well, for instance for AO, image enhancement, recognition/classification, risk management, predictive maintenance, auto-focus, guiding, biometry, etc. As an example, one can monitor the state of an optical system (artificial, like a telescope, or natural like an eye) on a regular basis for the sake of detecting some trend useful for patient management in ophthalmic (human eye), or predictive maintenance. In the case of biometry, one can analyze the engineered images retrieved from a given optical system sensing human specific natural or artificial features, such as, but not limited to, the eye, retina, cornea, iris, skin, fingerprints, ID code (1D or 2D), etc.

An Example: Telescope Optical Performance Analysis/Monitoring

One embodiment of the present invention is a method for analyzing a telescope optical performance on the field (or at the lab with an artificial star) using an actual star. In order to have a low-cost simple way, one may use an actual star, which is considered as a point source at the infinity and a defocused PSF of a known amount (engineering the image) at the level of an imaging camera (imager), here acting as the WF sensor, placed near the focal plane of a telescope.

The imager sensor plane can be located at some distance X from the scope focal plane using an absolute mechanical focuser with a high-resolution encoder. The focuser (e.g. a Crayford focuser) moves in or out the whole imager (and any associated devices) from the scope focal plane by a distance X chosen for making the proper engineered images and in relation with the telescope optics (focal length, aperture, etc.). Of course, it should be understood that another camera than the imager could be used for this task, like a guider, but the principle remains the same.

Figure 14:
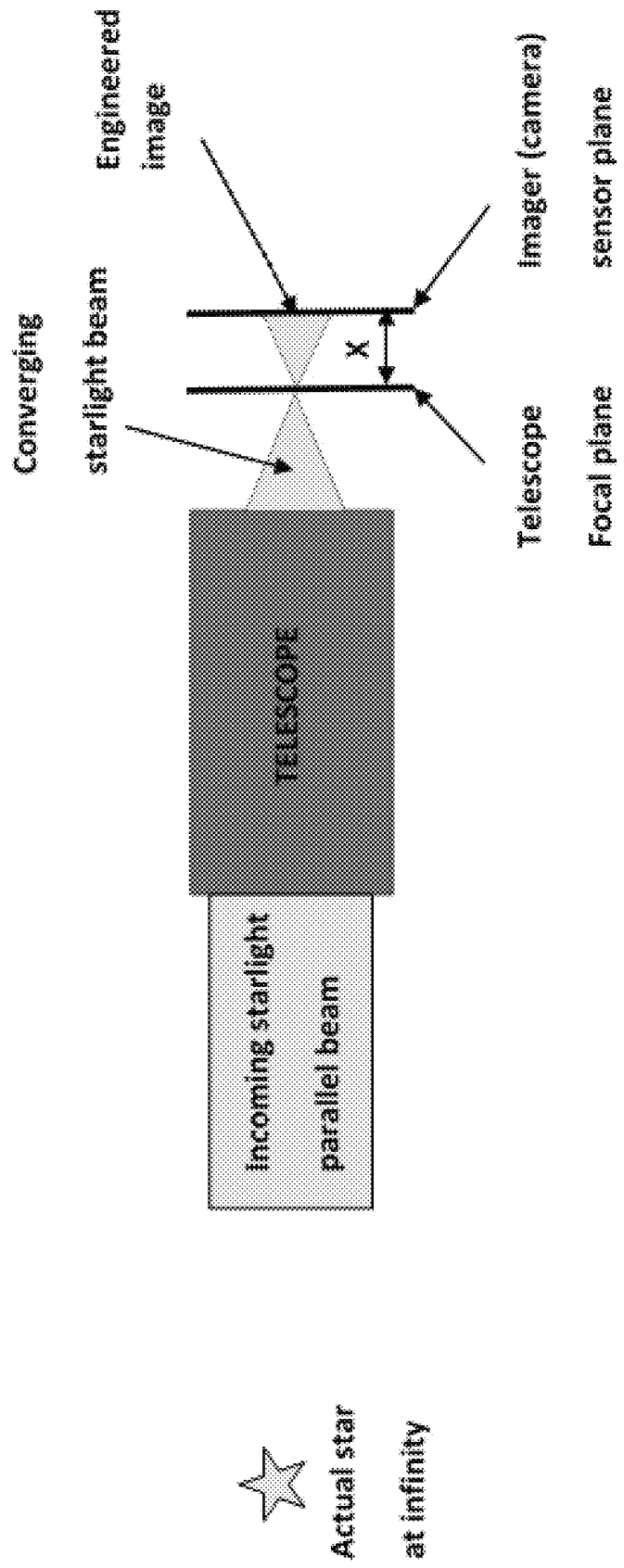
FIG. 14 is a diagram illustrating a telescope optical performance analysis with wavefront sensing and defocused point spread function as engineered image using an actual star, and wherein a focuser not shown.

FIG. 14 shows the apparatus for such scope optical analysis using an actual star. If one wants to use an artificial star, then this would be a double pass analysis, unlike with a natural one for which it is a single pass analysis. In both cases the inverse-model(s) outputs, the Zernike terms in the present invention for telescope optical performance analysis (again this is not a limitation in any way, form, or shape of the ideas and methods disclose in this document). In the context of using an artificial star, one may need to divide by two the Zernike terms because the double pass. In addition, if the artificial star is not designed such that it appears at infinity, then one may need to train a specific invers-model(s) for it. Otherwise, one could use the same model for both natural and artificial stars as long as one applies the right corrections to the Zernike terms due to the double pass situation with an artificial star.

In this example, one uses a single inverse-model (again this does not limit the scope of this document). In order to simulate engineered images, one needs first to choose a defocus value X (positive or negative) related to how much defocus optical wavefront error one wants to use for the task. Since one wants the inverse-model to be generic, in this example, (not associated with any given scope) one works on normalized units inside the unity circle. This means simulating a normalized scope with an aperture D=2 m therefore a radius R=1 m, for a wavelength lambda $\lambda$=1 m, and a focal length f=1 m. There are a denormalization steps for relating an actual telescope with the normalized one. The inverse-model outputs will be the Zernike terms for some of the Zernike polynomials for such normalized telescope as well as an estimation of the atmospheric turbulence (seeing) through the Fried's parameter r0.

From the inverse-model outputs, one can compute the following: the WF inside the unity pupil; the PSF at best focus (telescope focal plane), at any location, or under seeing limited conditions; and the Strehl ratio (SR). Much more information could be obviously computed from those Zernike terms and related wavefront decomposition, such as the MTF, contrast function, and telescope optical misalignment, when the optical scope layout is known. In the latter case from the telescope data or from a database of many scopes describing their optical and mechanical layouts, one can use such scope layout information/data, the Zernike terms, and related aberrations from the inverse-model outputs in order to decide and/or to act on the telescope mechanical devices for aligning (known as collimation in the field of telescope) its optics (tilt/tip offset, optical element spacing, etc.). This can be done by somebody or automatically with actuators on the telescope. In some applications, the telescope under analysis is an assembly of optical parts still under production, and the resulting WF analysis could be used then to feed back the necessary information for the production, which could lead to corrections/adjustments of the optical surfaces and elements themselves (like polishing and/or coating) and/or adding/removing optical and/or mechanical elements.

In order to train and to test/validate the inverse-model, one simulates many different aberrations and scope central obstruction (secondary mirror) as well as seeing conditions (phase errors and scintillation). One defines the possible variations for each Zernike coefficient range, say +/− some wave errors (rms or PV), and a range for seeing r0 and scintillation as well as a range for the scope central obstruction (zero would be used for a refractor telescope while some positive number, between 0 and 1, is used for a reflector telescope). Those ranges are then applied randomly (using some statistical distributions, uniform, Gaussian, or others with or without correlations between the various terms) to simulate many engineered images, say millions.

In this example, the engineered images are defocused PSFs computed from the following Zernike terms: Z1 (tilt); Z2 (tip); Z3 (defocus); Z4 (oblique astigmatism); Z5 (vertical astigmatism); Z6 (vertical coma); Z7 (horizontal coma); Z8 (spherical 3rd order); Z9 (vertical trefoil); and Z10 (horizontal trefoil). Higher order Zernike polynomial are ignored in this example.

One considers uncoherent light and choses only one wavelength λ (e.g. 550 nm for the visible band during the denormalization step) for the inverse-model. However, one could have simulated the data and trained the inverse-model with more than one wavelength at a time or combined denormalized data for several single wavelengths if one wishes.

Since the light is supposed to be uncoherent, the Z0 (piston) term is ignored here. For making the inverse-model more general and usable for refractor telescopes as well as reflector telescopes, one uses the orthonormal annular Zernike polynomials with a central obstruction e, if any, defined as the ratio between the scope aperture D and the central obstruction d, hence e=D/d. Therefore, e is a number between 0 and 1, and the astronomical seeing is defined by the Fried's parameter r0.

Inverse-Model

Building an inverse-model uses the following ranges, while assuming that engineered images are made with defocused PSFs of +5 waves RMS:

e=0 to 0.5 (cover refractor and most reflector telescopes)
Z1=+/−2.1 wave RMS
Z2=+/−2.1 wave RMS
Z3=4.1 to 5.9 wave RMS (5+/−0.9 wave RMS to simulate measurement errors)
Z4=+/−0.3 wave RMS
Z5=+/−0.3 wave RMS
Z6=+/−0.3 wave RMS
Z7=+/−0.3 wave RMS
Z8=+/−0.3 wave RMS
Z9=+/−0.3 wave RMS
Z10=+/−0.3 wave RMS The Zernike RMS coefficient ranges have been chosen to cover a realistic range of possible optical aberrations due to optical misalignment (collimation error) of the telescope in this example. Any range could have been chosen, and we could have used more or less Zernike coefficients (orders) to be involved in this simulation. The random generation of those above values is done with a uniform distribution across their ranges. Other distributions, or mix of those, like a Gaussian, could have been used as well.

As a first step, each simulated engineered image is made of a set of random values using the above ranges for building a normalized wavefront phase function $\Phi(x,y)$ inside the unity circle pupil with central obstruction e, a random value itself, using the orthogonal annular Zernike polynomials. In order to insure enough resolution for this wavefront simulation and consecutive PSF calculation (using an 2D FFT as the 2D Fourier transform), one uses N=1024 points (or samples) with a spatial period of ds=1/100, or a 200th of the telescope diameter (set at 2 for an unity circle pupil, R=1). Of course, other values can be used as well, and this is only one possible choice among many designs for providing enough simulation accuracy while limited memory and computer power.

Figure 15:
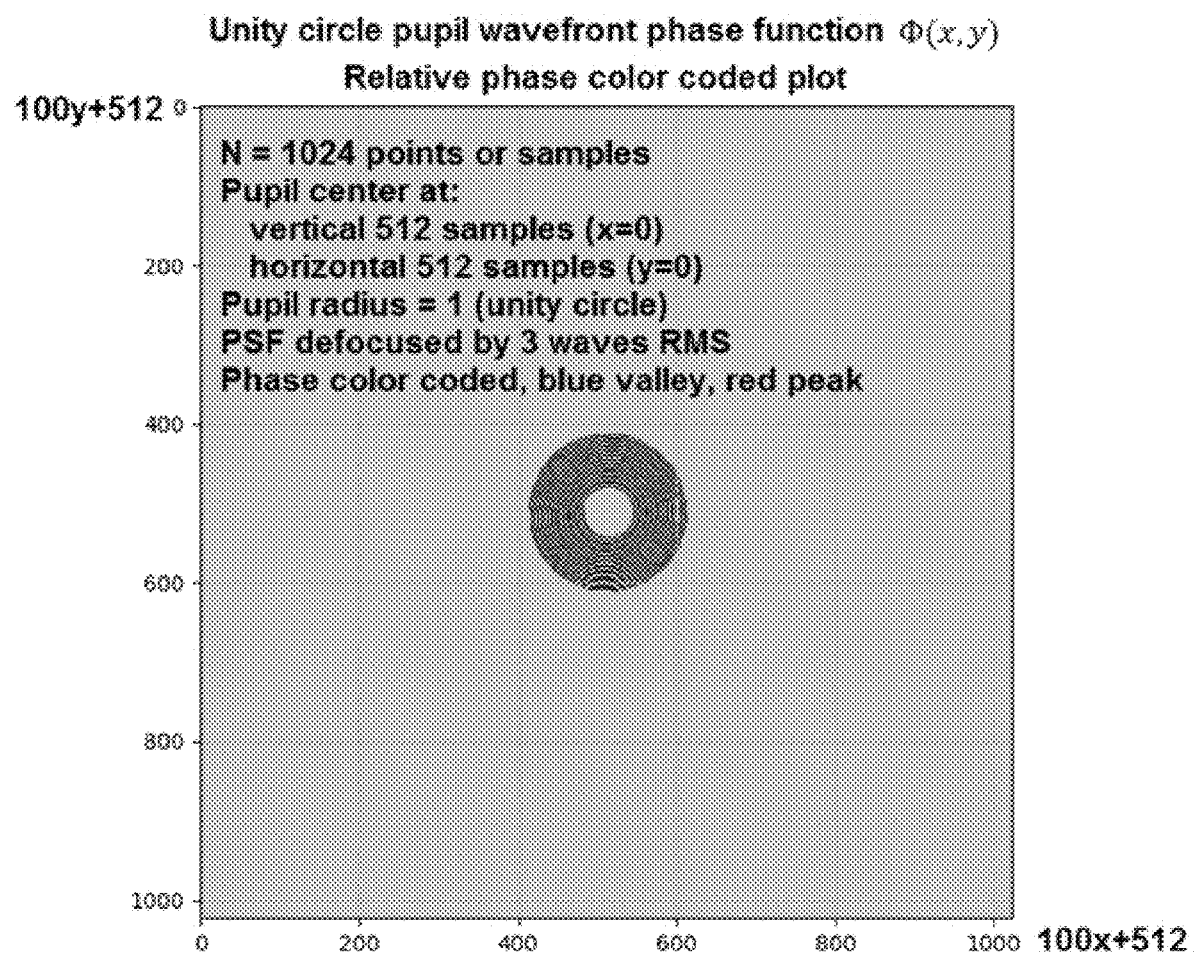
FIG. 15 is a diagram illustrating a unity circle pupil wavefront wrapped phase function for ds=1/100, N=1024, wherein the phase is shown in color-coded relative values (i.e. red for peak and blue for valley) such as e=3 (30% central obstruction) and Z3 engineered defocus 3 waves RMS, and wherein the second step in the simulation of an engineered image is the calculation of the point spread function related to the wavefront phase function from the first step, and wherein the point spread function is the squared of the Fourier transform of the wave front phase function.

FIG. 15 shows a typical random WF phase function for the above parameters with a defocus of 3 wave RMS (Z3) in this case. The pupil center is located at 512 samples in horizontal and vertical axes. The unity circle radius is 100 samples wide. The PSF is defocused (before any random variation of Z3) by 5 waves RMS, which translates to 10.39 waves at the edge of the pupil. This creates a quadratic phase shape which is shown in FIG. 15 with alternate rings each time that the wavefront phase passes a multiple $2\pi$, or one wave (in this figure the phase is wrapped), and there are 10 complete rings. The other patterns in the wavefront phase function are related to random aberration for the above Zernike annual coefficients chosen randomly. With this choice of ds and N, the simulated phase function exceeds the pupil. Values outside the pupil are set to zero.

$$PSF(u,v)=|\Im_{2D}(\Phi(x,y))|^2$$

... where $\Im_{2D}(\cdot)$ is the 2D Fourier transform computed inside the unity circle.

The PSF u and v units are normalized radians. The quantification step (one sample) is given by 1/(N*ds)=100/1024=0.0977 radian. The diffraction limit (DL) of the normalized telescope used for the simulation is 1.22 radians (f=1, R=1, λ=1). There are about 13 samples inside the DL angle, however, the PSF is defocused by many waves and therefore much wider, about 40 radians, or about 410 samples, as shown in FIG. 15, as an example for a 3 waves RMS defocus (Z3). At this stage, one may add the effect of the astronomical seeing, and the Fried's parameter r0 is chosen randomly (uniformly) from 45 mm to 90 mm. Moreover, as can be seen in FIG. 15, the defocused PSF under seeing limited conditions (r0=45 mm) is shown on the left, and the defocused PSF without any seeing (from space) is shown on the right.

Figure 16:
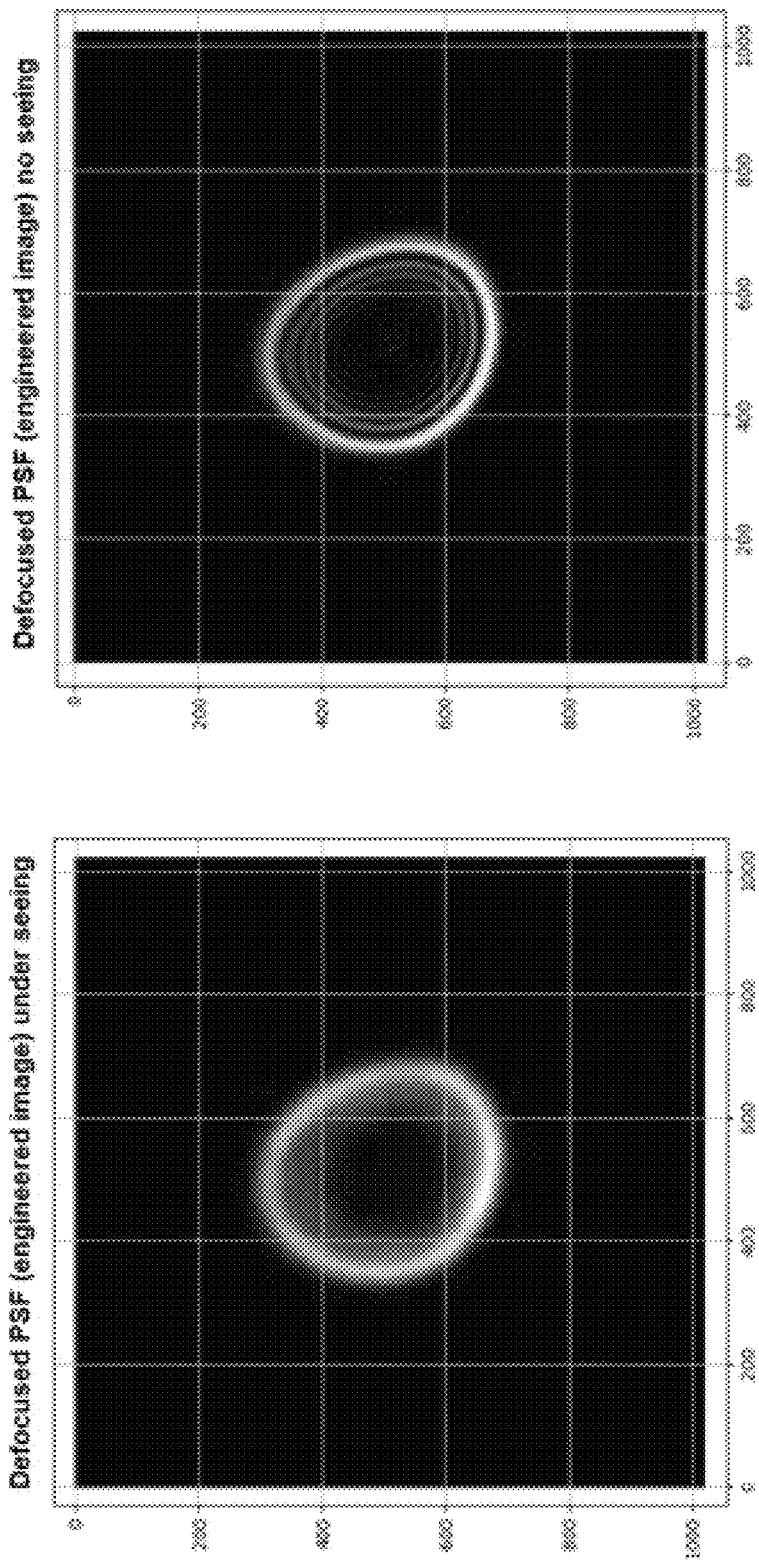
FIG. 16 is a diagram illustrating an aberrated defocused PSF by 3 waves RMS (engineered image) computed from the 2D FFT (1024×1024 points) squared modulus using the figure wavefront phase function shown in FIG. 15.

The engineered images are considered long term exposures under seeing limited conditions. Using the Kolmogorov's atmospheric turbulence model, one can create a phase mask for a given r0. For completeness, scintillation is also estimated and simulated by Gaussian random fluctuations of the wavefront amplitude inside the pupil according to the Kolmogorov theory and related r0 values. The defocused PSF is computed using a 2D FFT (1024×1024 points). FIG. 16 shows the defocused PSF (with its set of random aberrations and Z3 defocused set at 3 waves RMS) both before and after the introduction of the seeing effect discussed above for r0=45 mm (average seeing for most people) and e=3 (30% central obstruction).

The third step is to build two databases and to train the inverse-model. There is one database with M randomly engineered images (defocused PSFs) and one database with the M associated desired values (r0 and the Zernike coefficients/terms in this example). The first database is the input for the inverse-model training/validation, and the second database is the outputs for its training/validation.

Figure 17:
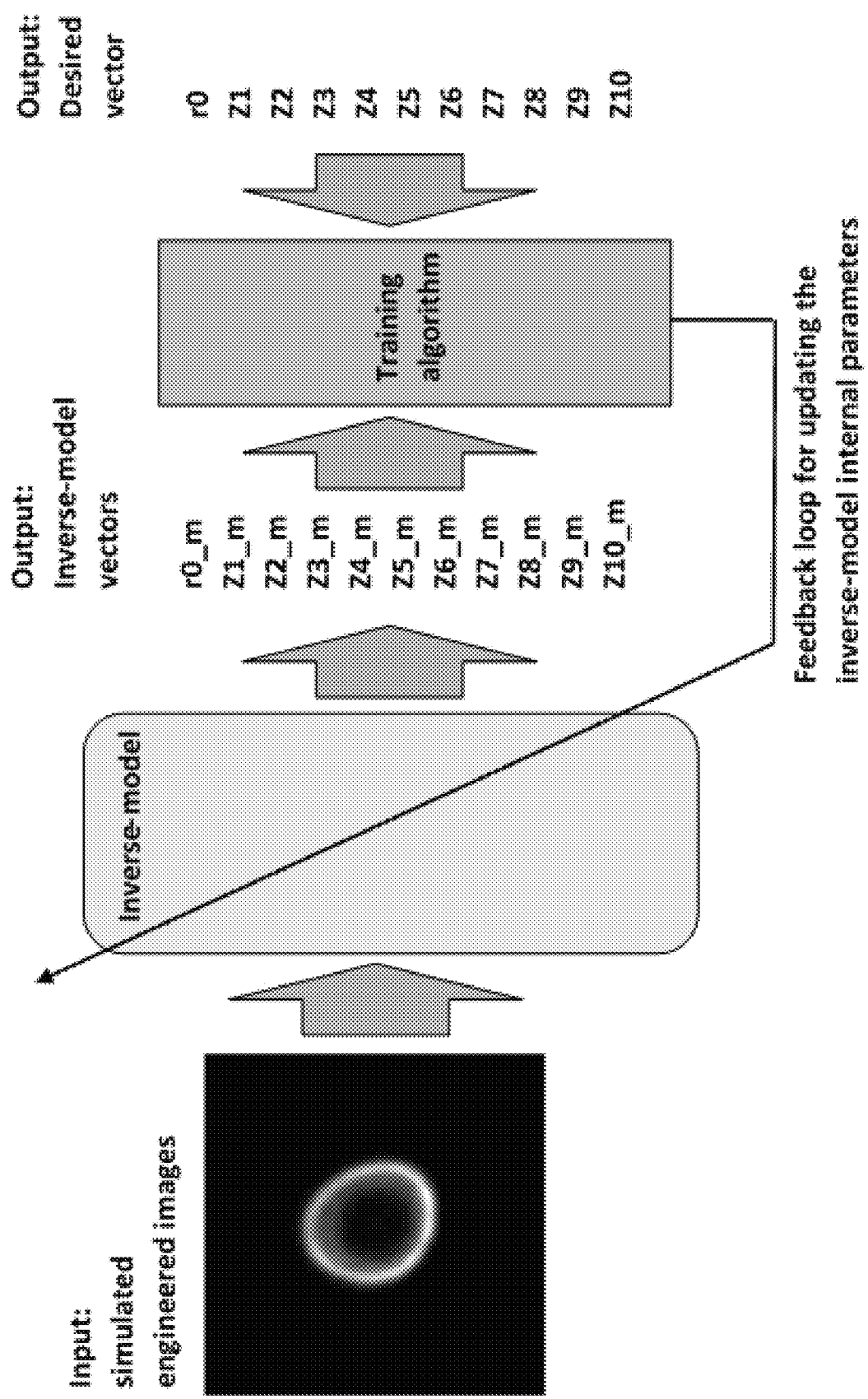
FIG. 17 is a diagram illustrating the concept of training a wavefront sensing inverse-model.

FIG. 17 shows the inverse-model training concept. Randomly simulated engineered images are fed to the inverse-model input while corresponding desired output vectors, made of the random values used to simulate the corresponding engineered images, are fed to a training algorithm which compare those, using some metric (like least mean squared errors) against the corresponding inverse-model outputs (estimations, or best "guess" from the inverse-model for the corresponding inputs). In addition, the training algorithm updates the internal parameters of the inverse-model using a feedback loop (usually iteratively) until some accuracy metric value is met (like the mean absolute or quadratic error) and/or some amount of iteration has been reached or some combinations of both or other machine learning methodologies. Typically, a second set of databases is simulated to validate the model against new data unseen during the training phase yet belonging to the same process. Such validation step can be used to further refine the inverse-model.

It should be understood that for anybody skilled in the field of machine learning, there are many various ways to accomplish the training and optimization of the inverse-model(s), likewise there are many different possible inverse-models learning methods including, but not limited to, artificial neural networks (shallow as well as deep learning network architectures), support vector machines using various activation functions/kernels, as well as feature vector machines, statistical multivariate regressions, linear or not, genetic algorithms, or any combinations thereof.

Use of the Inverse-Model and Denormalization

After having successfully trained and built an inverse-model(s) for a given task, like the example described above, one can use it to provide WFS information for any given new (unknown during the training/validation phase) engineered images (simulated or actual). The inverse-model is presented with a new engineered image (or many at once if one uses more than one engineered image for analysis of a given optical system, like defocused PSFs from different locations in the optical path) unseen before. The inverse-model then outputs estimations of the related engineered image(s) of WF information, such as, but not limited to, a set of Zernike coefficients and Fried's parameter r0, as in the example above with telescopes. This information may be used to, but not limited to, reconstruct a good estimation of the actual wavefront phase function, PSF, optical transfer/property function, MTF, SR, Seidel's aberrations, ophthalmic data, biometric data, or any other relevant data and figures of merit including direct information on a given optical system layouts, such as collimation (alignment) information for advising, displaying, recording, sharing, monitoring, doing preventive maintenance, or acting upon.

In the above WFS for telescope example context, to be able to actually analyze a given telescope, one needs to defocus the PSF for making the expected engineered image (again this is just an example without limiting the scope of the present invention). For the present invention, one uses the metric system, distances are express in meter [m], or their multiple/submultiples. The defocus in this example is accomplished by moving the imaging camera at some distance (offset) X from the telescope focal plane. The relationship between the focuser offset value X (distance between the scope focal plane and imager sensor plane as can be seen in FIG. 14) and the optical path difference (OPD) at the edge of the pupil is given, in very good approximation (small angle), by:

$$X = 8 \cdot OPD \cdot (F/\#)^2$$

... where $F/\# = DF^{-1}$ is the scope f-number.

The defocus orthonormal annular Z3 coefficient (expressed in RMS value) is related to the OPD by $Z3 = OPD \cdot (2\sqrt{3})^{-1}$, for any e. For instance, if one chooses a +10 waves PV defocus at $\lambda = 550$ nm, then:

$$Z3 = 10 \cdot 550 \cdot 10^{-9} \cdot (2\sqrt{3})^{-1} = 1588 \text{ nm or } 2.89 \text{ RMS wave}$$

In this example, one sets Z3=+5 waves RMS (see simulation range in section "Inverse-model") or 2750 nm, about +17 waves PV, while analyzing a reflector telescope with D=254 m (10"), e=0.45, f=2.032 m, leading to F/#=8, at $\lambda = 550$ nm the resulting focus offset X is:

$$X = 8 \cdot (5 \cdot 2\sqrt{3}) 550 \cdot 10^{-9} 8^2 = 0.04878 \text{ m}$$

... or 4.878 mm.

Therefore, one should move the focuser 4.9878 mm outward (since X is a positive value in this case, however, we could have used a negative defocus, like −5 waves RMS leading to a negative X value for which the focuser would move inward) from the telescope focal plane.

Once one has taken a long exposure (few minutes for averaging out the seeing) of a given defocused actual bright star in the sky to get our engineered image, one can use it as the input of our trained inverse-model. However before doing so, one needs to match this image resolution (pixel and size) with the simulated 1024×1024 pixels engineered images used for the training. This is where the denormalization process takes place since all the simulations, in this example, have been done inside the unity circle assuming a normalized telescope with f=1, D=2, and $\lambda = 1$.

From the angular resolution of the simulated engineered images (defocused PSFs):

$$\alpha_s = \frac{1}{N * ds} = \frac{100}{1024} = 0.0977 \text{ radian}$$

one computes the simulated pixel size $p_s$ for the telescope under analysis. This is done by a denormalization formula including the scope aperture, focal length, and the wavelength at which the analysis is conducted/desired. In the case of a polychromatic light analysis, like in this example, one may use an average wavelength for the visible band, say 550 nm, or one may use several wavelengths across the band and do the related denormalizations for computing the related WFs and then sum them. In this example, we will use a single wavelength (550 nm) approach, which is usually a good enough approximation under seeing limited conditions.

$$p_s = 2\alpha_s \lambda (F/\#) = 2 \cdot 0.0977 \cdot 550 \cdot 10^{-9} \cdot 8 = 8.6 \cdot 10^{-7} \text{m}$$

... or 0.86 microns at the telescope focal plane. This means that the total field of view (FOV) for the simulated engineering images is $1024 \cdot 8.6 \cdot 10^{-7} = 8.8 \cdot 10^{-4}$ m, or 880 microns. With a 5 wave RMS defocus (Z3), the defocused PSF diameter (engineered image) is about 610 microns wide, or 70% of this FOV.

Figure 18:
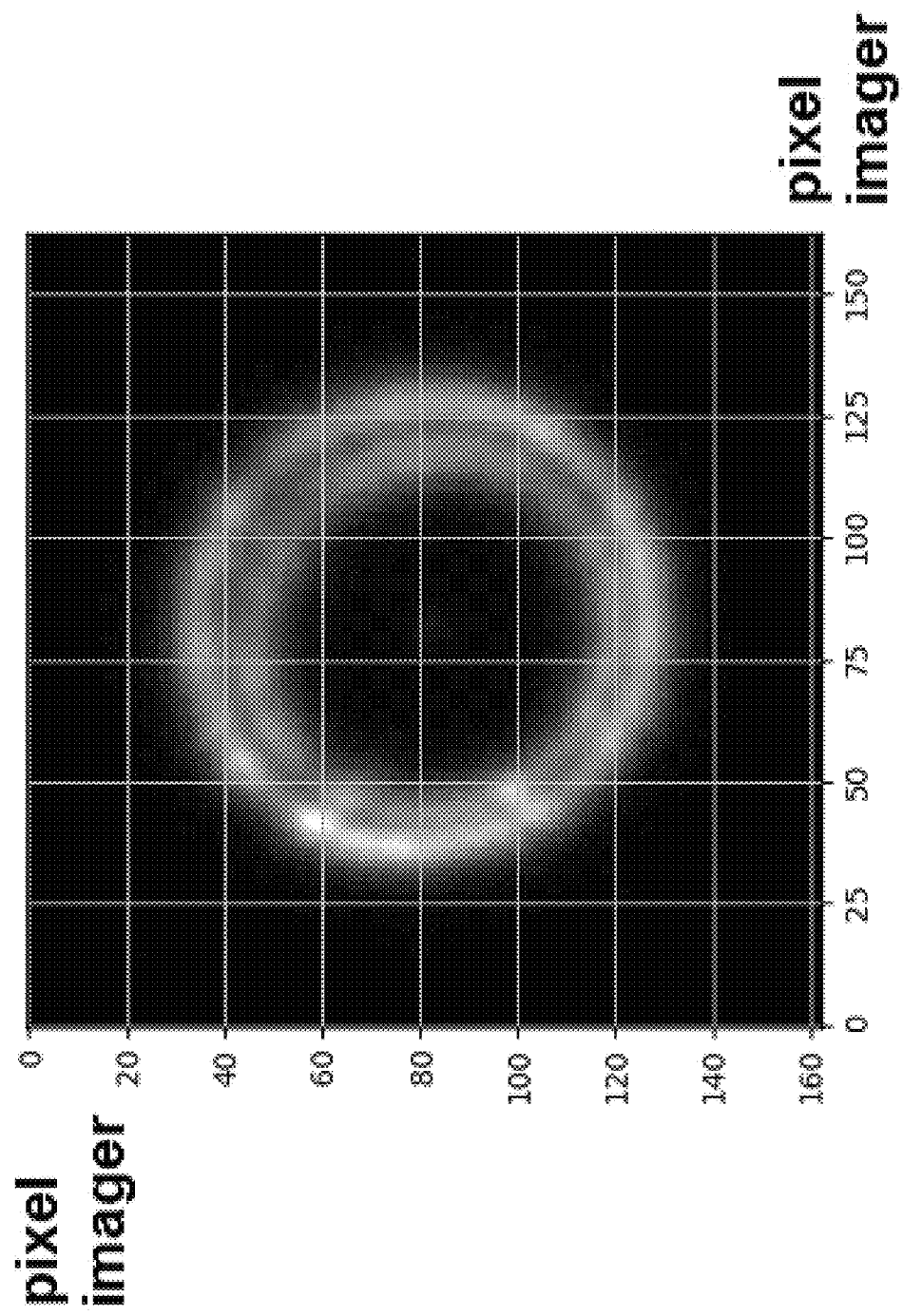
FIG. 18 is a depiction showing an actual engineered image (defocus point spread function) under seeing limited conditions with a 2 minutes exposure time by 163×163 imager pixel wide.

The actual camera used for imaging (the imager) the engineered images (defocused PSFs) features squared pixels of 5.4 microns. Therefore, the size in pixel of the imager FOV matching the simulated engineered images FOV is 880/5.4=163 pixels (imager) wide. In order to feed our inverse-model with any observed/actual engineered image from the imager, one can resize the imager FOV of 163×163 pixels (in this example) to the simulated engineered image FOV used for the training of the inverse-model, 1024×1024 pixels with any suitable digital image processing resizing algorithms. It should be understood that resizing (interpolation/decimation) images can be done by many ways which are well known to anybody skilled in the field of digital image processing. FIG. 18 shows one example of an actual engineered image taken by such a telescope with such imager under seeing limited conditions. The image was exposed 2 minutes to average out the seeing while the focuser was set to be at 4.878 mm away from the telescope focal plane.

As can be seen in FIG. 18, one can readily and clearly spot at least some level of coma (at 45 degrees across the FOV from left to right). The image in FIG. 18 is affected by the seeing, including some scintillation. The image in FIG. 18 was also fed to a trained inverse-model (an artificial neural network) using the r0 and Zernike coefficient ranges discussed in section "Inverse-model". This led to the following results ($\lambda$=550 nm):

r0=58.6 mm (This is consistent with the local seeing of the test site which was about 2 arc-second (") FWHM that night.)

Z1=452 nm RMS (This value will be ignored, set to zero for the WF reconstruction.)

Z2=−126 nm RMS (This value will be ignored, set to zero for the WF reconstruction.)

Z3=2694 nm RMS (This value is close to the 5 waves RMS (2750 nm) defocus used.)

Z4=−3.04 nm RMS
Z5=−82.3 nm RMS
Z6=−10.4 nm RMS
Z7=45.3 nm RMS
Z8=2.5 nm RMS
Z9=−2.78 nm RMS
Z10=48.8 nm RMS

Figure 19:
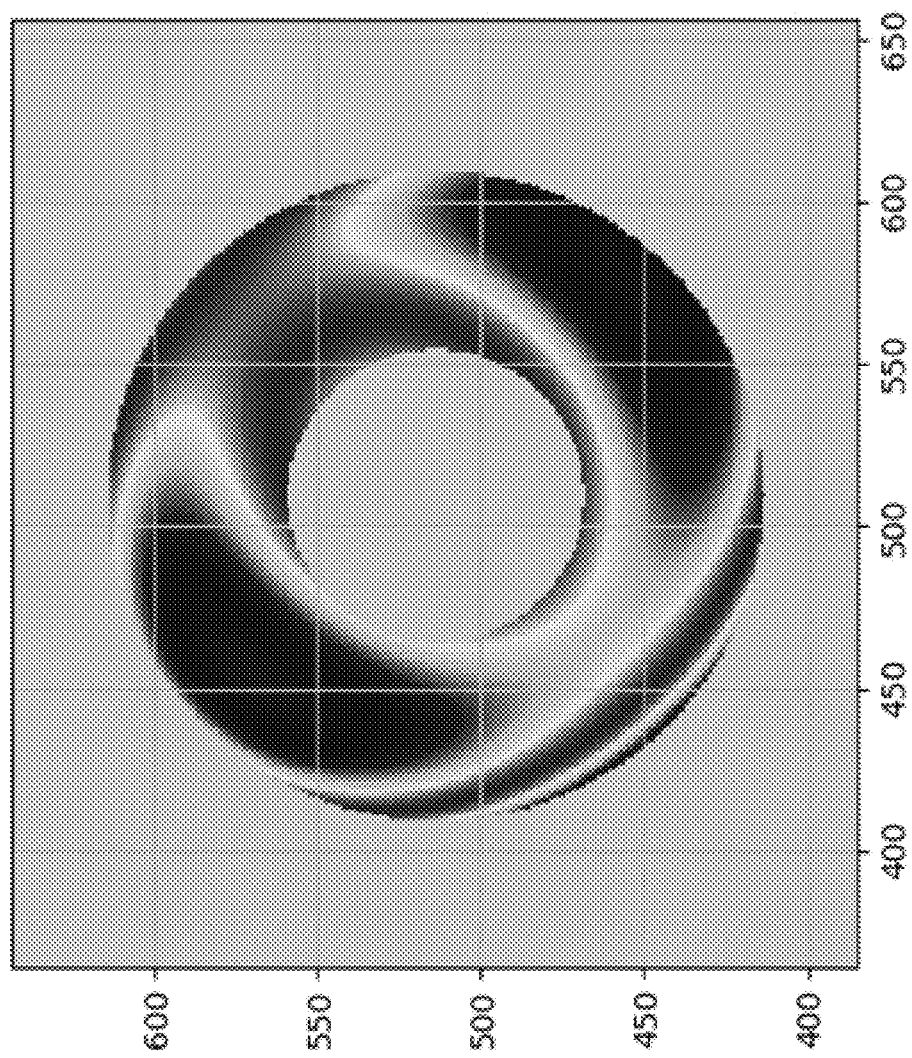
FIG. 19 is a depiction illustrating a telescope wavefront phase function, at focal plane (no seeing), reconstructed from the Zernike coefficients output by the inverse-model fed by the engineered image (defocused point spread function) from FIG. 18 after proper resizing, wherein the red is the peaks of the WF and the blue is the valleys of the WF.

Using the orthonormal annular Zernike coefficients, one can reconstruct the telescope wavefront (and/or any other relevant figures of merit) for an actual star at the scope focal plane (setting Z1, Z2, and Z3 to zero) without any seeing effect (like from space). The corresponding wavefront is shown by the FIG. 19 as a color-coded image, wherein the red is the peaks of the WF and the blue is the valleys of the WF.

Figure 20:
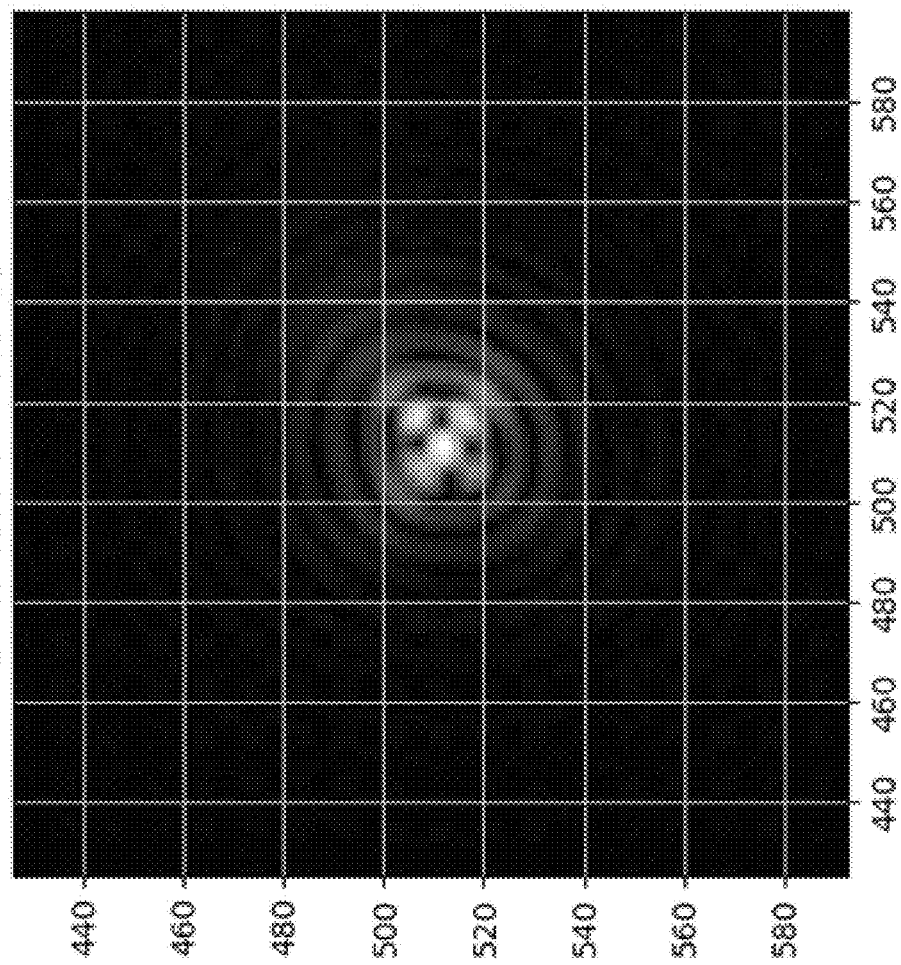
FIG. 20 is a depiction illustrating a telescope point spread function, at focal plane, 550 nm, and no seeing.

One can use this reconstructed WF to compute the telescope PSF (at the focal plane) without any seeing effect (like from space) and compute the Strehl ratio (SR). FIG. 20 shows the reconstructed PSF as it would look from space when using an actual star.

As can be seen in FIG. 20, one can clearly see the astigmatism and coma. This telescope needs some optical alignment (collimation). Using all of the inverse-model output data, including defocus (Z3) and seeing (r0), while setting Z1 and Z2 at zero, one can reconstruct the engineered image (defocus PSF) and compare with the actual one in FIG. 18 used for this analysis.

Figure 21:
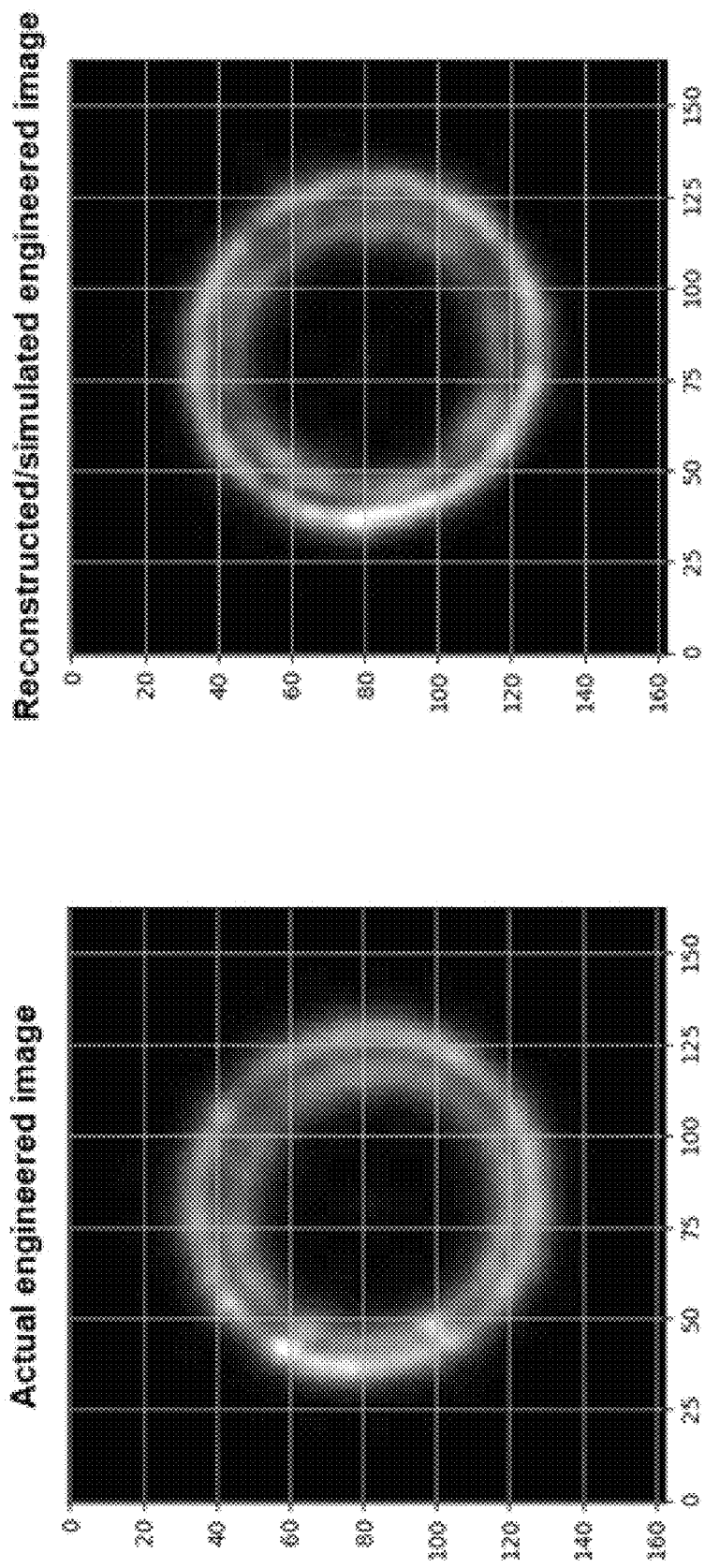
FIG. 21 is a depiction illustrating an actual engineered image (on the left) versus a reconstructed engineered image, including seeing simulation, (on the right), wherein each image is 163×163 pixels.

On the left of FIG. 21 is the actual engineered image taken by the imager (2 minutes exposure time). Moreover, on the right of FIG. 21 is the reconstructed engineered image including seeing simulation using the r0 value from the inverse model. Both images in FIG. 21 look very similar. However, the reconstrued engineered image does not show the secondary mirror spider diffraction patterns (seen in the left image) which were not used/known by the inverse-model, but it could have.

The secondary mirror diffraction patterns are very small and difficult to spot on a seeing limited conditions image for this telescope. However, under different conditions (lab for instance), or with different telescope, those may impact the results. Those could also be simulated while computing the engineered images for the inverse model training if necessary or required. As a matter of fact, and as disclosed before, one can tailor the inverse-model(s) and related training databases for any given optical layout (natural and/or artificial), either in real-time or offline. Even though in our example, we trained the inverse-model to be generic across a large range of telescopes, however, one can also be very specific and focus in a given (or subset of) optical system.

Again, it should be understood that we used a telescope for our example but this is not a limitation of the disclosed ideas and methods in this document in any way, from or shape. For instance, one could use the apparatus, or an equivalent optical system, illustrated in the FIG. 10 for analyzing an eye and for training an inverse-model(s) using simulated engineered images and data, as well as building the corresponding engineered images and databases, for some kind of eyes, like human eyes, or cat eyes, of even a (or subset of) category of eye, such as human (or others) eyes with presbyopia, myopia, and others. As a consequence, the inverse-model(s) could be used for biometric identification of someone, if it was training for that matter, using either the eye or other biometric information with the appropriate optical systems.

Example of WF Field Analysis

Figure 22:
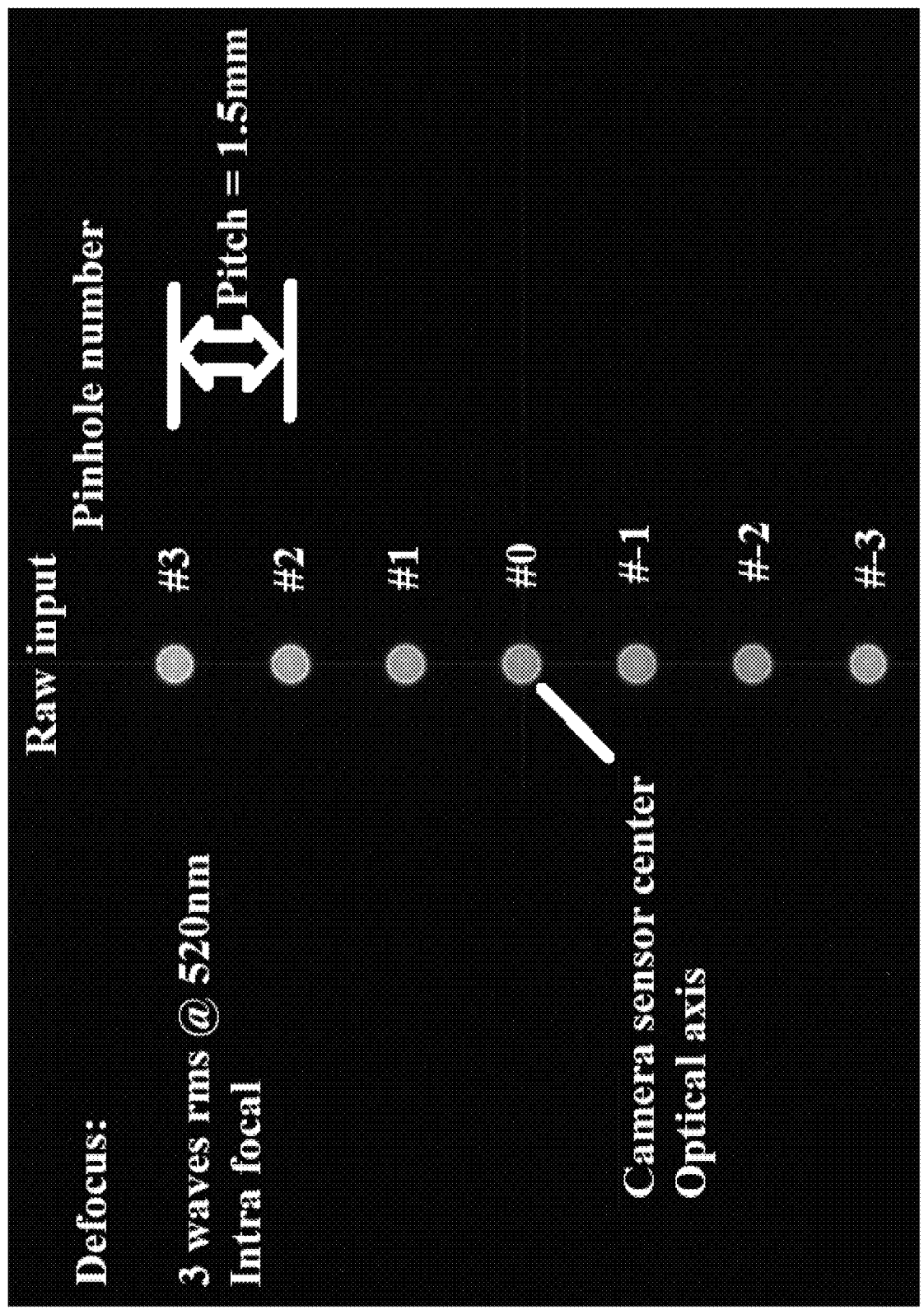
FIG. 22 is a diagram illustrating a multi-points source engineered image, for field dependent WFS.
Figure 23:
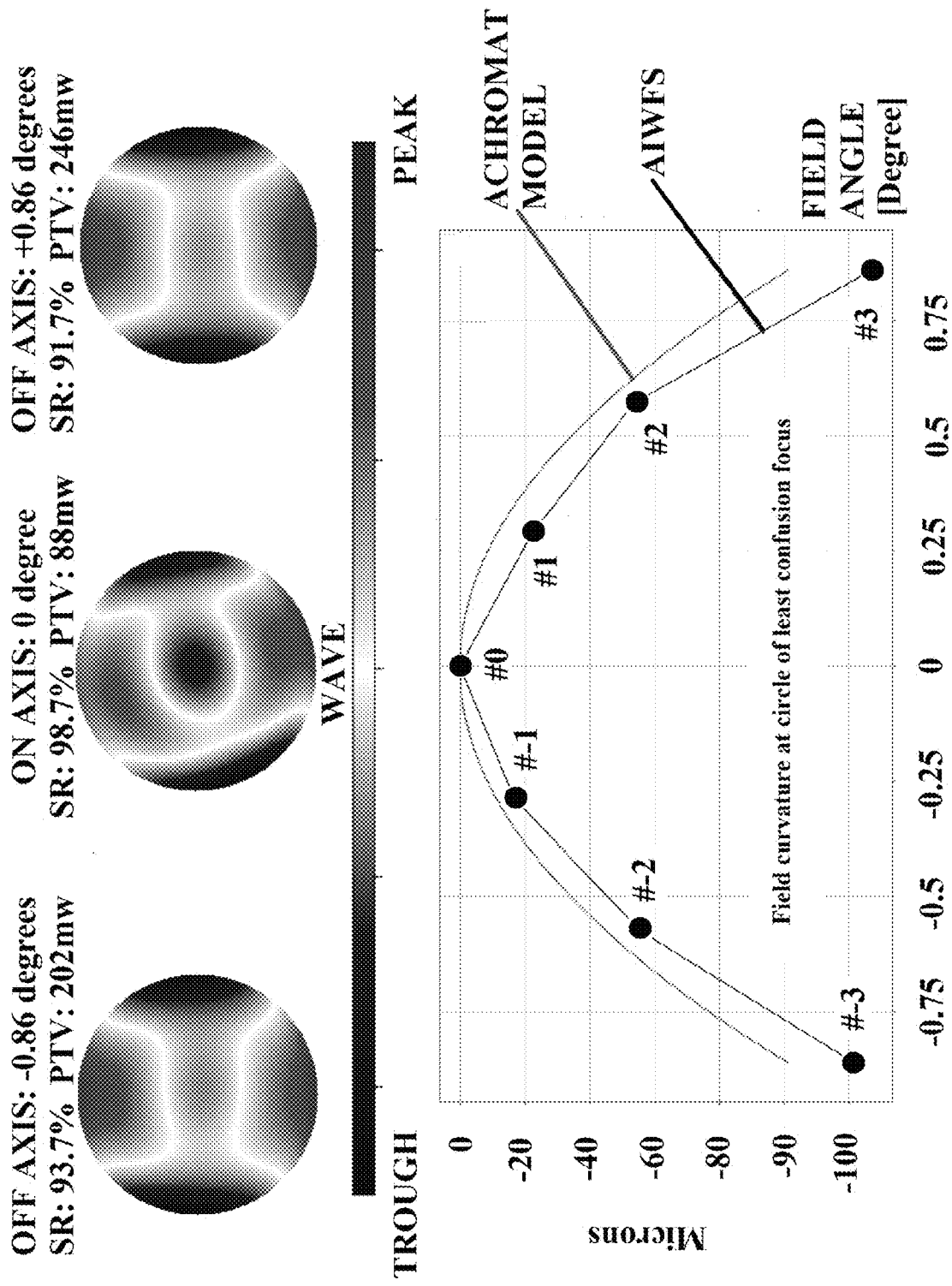
FIG. 23 is a diagram illustrating a field curvature at circle of least confusion focus.

The example shown in FIGS. 22 and 23 is a WF field analysis with on and offset axis at cone, in real time with a single image, one camera, and no part in motion. FIG. 22 further shows hardware with 7 pinholes, each with a diameter of 10 microns and a pitch of 1.5 mm.

FIG. 23 shows a field dependent WF sensing (related to the above multi-points source) for a 24 mm @ f12.5 achromatic refractive telescope. The top portion of FIG. 23 further shows, from left to right, −4.5 mm off axis WFS, on axis WFS, +4.5 mm off axis WFS. The bottom portion of FIG. 23 further shows a field curvature at circle of least confusion focus using the 7 pinholes WFS data (in read achromat model, in black WFS data).

Although the invention has been explained in relation to its preferred embodiment, it is to be understood that many other possible modifications and variations can be made without departing from the spirit and scope of the invention as hereinafter claimed.

What is claimed is:

1. A method of wavefront sensing with engineered images, the method comprises the steps of:

(A) providing at least one wave receiving system, wherein the wave receiving system is associated with at least one corresponding environment, wherein the wave receiving system is a computerized imager of an optical device, and wherein the wave receiving system is configured to perform phase diversity with at least one engineered image;

(B) designating at least one desired parameter range for the optical device with the computerized imager, wherein the desired parameter range relates to at least one optical performance metric for the optical device;

(C) simulating at least one preliminary phase-diversity engineered image to correspond with the desired parameter range with the computerized imager, wherein the preliminary phase-diversity engineered image is computed from an aberrated wavefront expressed in terms of aberration phase errors within the desired parameter range;

(D) generating at least one inverse-model with the computerized imager, wherein the inverse-model outputs the desired parameter range by inputting the preliminary phase-diversity engineered image;

(E) executing a training process for the inverse-model to readily and accurately output the desired parameter range with the computerized imager or at least one external computing site by inputting the preliminary phase-diversity engineered image;

(F) receiving at least one measurement phase-diversity engineered image with the computerized imager, wherein the measurement phase-diversity engineered image is computed from another aberrated wavefront expressed in terms of aberration phase errors within the desired parameter range; and (G) outputting at least one estimated parameter value for the wave receiving system with the inverse-model with the computerized imager by inputting the measurement phase-diversity engineered image into the inverse-model.

2. The method of wavefront sensing with engineered images, the method as claimed in claim 1, wherein the preliminary phase-diversity engineered image and/or the measurement phase-diversity engineered image is configured from a mean of defocusing.

3. The method of wavefront sensing with engineered images, the method as claimed in claim 1, wherein the preliminary phase-diversity engineered image and/or the measurement phase-diversity engineered image is configured from a mean of the wave receiving system while using at least one wave aberration element.

4. The method of wavefront sensing with engineered images, the method as claimed in claim 3, wherein the wave aberration element is at least one refractive element, at least one reflective element, at least one diffractive element, or combinations thereof.

5. The method of wavefront sensing with engineered images, the method as claimed in claim 1, wherein the desired parameter range and/or the estimated parameter value is defined by Zernike polynomials, Strehl's ratio, Seidel's aberrations, a point spread function, an optical transfer function, optomechanical data, ophthalmic measurement data, wavefront, or combinations thereof.

6. The method of wavefront sensing with engineered images, the method as claimed in claim 1 comprises the steps of:
providing the wave receiving system with at least one wave modifying element, wherein the wave modifying element is associated with the estimated parameter value;
generating at least one alignment instruction for the wave modifying element in accordance to the estimated parameter value after step (G); and
executing the alignment instruction for the wave modifying element.

7. The method of wavefront sensing with engineered images, the method as claimed in claim 1 comprises the step of:
locally executing the training process for the inverse-model with the computerized imager during step (E).

8. The method of wavefront sensing with engineered images, the method as claimed in claim 1 comprises the step of:
remotely executing the training process for the inverse-model with the external computing site during step (E).

9. The method of wavefront sensing with engineered images, the method as claimed in claim 1, wherein the training process for the inverse-model is configured with edge computing, stream computing, cloud computing, batch computing, or combinations thereof.

10. The method of wavefront sensing with engineered images, the method as claimed in claim 1, wherein the inverse-model is configured as an artificial neural network, a support vector machine, a multi-variate statistical regression, or combinations thereof.

11. The method of wavefront sensing with engineered images, the method as claimed in claim 1 comprises the steps of:
providing at least one wave source;
capturing the wave source as at least one new image with the computerized imager;
modifying the new image to analyze the wave receiving system in relation the corresponding environment; and
designating the new image as the preliminary phase-diversity engineered image during step (C).

12. The method of wavefront sensing with engineered images, the method as claimed in claim 11, wherein the wave source is configured as a point source or an extended source.

13. The method of wavefront sensing with engineered images, the method as claimed in claim 11, wherein the wave source is generated by a natural source or an artificial source.

14. The method of wavefront sensing with engineered images, the method as claimed in claim 11, wherein the wave source is made of coherent light or incoherent light.

* * * * *